US012800545B2

(12) United States Patent
Dehlinger et al.

(10) Patent No.: US 12,800,545 B2
(45) Date of Patent: *Nov. 17, 2026

(54) SYSTEMS AND METHODS FOR DECODING PIXEL SIGNALS FOR BASE CALLING NUCLEIC ACIDS

(71) Applicant: ILLUMINA, INC., San Diego, CA (US)

(72) Inventors: Dietrich Dehlinger, San Francisco, CA (US); Ali Agah, Menlo Park, CA (US); Tracy Helen Fung, San Francisco, CA (US); Emrah Kostem, Menlo Park, CA (US)

(73) Assignee: ILLUMINA, INC., San Diego, CA (US)

( * ) Notice: Subject to any disclaimer, the term of this patent is extended or adjusted under 35 U.S.C. 154(b) by 1024 days.

This patent is subject to a terminal disclaimer.

(21) Appl. No.: 17/970,504

(22) Filed: Oct. 20, 2022

(65) Prior Publication Data

US 2023/0039010 A1 Feb. 9, 2023

Related U.S. Application Data

(63) Continuation of application No. 17/831,424, filed on Jun. 2, 2022, now Pat. No. 11,953,464, which is a continuation of application No. 16/241,902, filed on Jan. 7, 2019, now Pat. No. 11,378,544.

(60) Provisional application No. 62/614,930, filed on Jan. 8, 2018, provisional application No. 62/614,934, filed on Jan. 8, 2018.

(30) Foreign Application Priority Data

Apr. 12, 2018 (NL) ..................................... 2020758

(51) Int. Cl.

| | |
|---|---|
| ***G01N 27/414*** | (2006.01) |
| ***B01L 3/00*** | (2006.01) |
| ***B01L 7/00*** | (2006.01) |
| ***C12Q 1/6869*** | (2018.01) |
| ***C12Q 1/6874*** | (2018.01) |
| ***G01N 21/64*** | (2006.01) |
| ***G01N 21/76*** | (2006.01) |
| ***G06F 18/24*** | (2023.01) |
| ***G06V 10/75*** | (2022.01) |
| ***G16B 30/00*** | (2019.01) |

(52) U.S. Cl.

CPC .... *G01N 27/4145* (2013.01); *B01L 3/502715* (2013.01); *C12Q 1/6874* (2013.01); *G01N 21/6454* (2013.01); *G06F 18/24* (2023.01); *G06V 10/751* (2022.01); *B01J 2219/00711* (2013.01); *B01J 2219/00722* (2013.01); *B01L 7/52* (2013.01); *B01L 2200/147* (2013.01); *B01L 2300/0636* (2013.01); *B01L 2300/0645* (2013.01); *B01L 2300/0663* (2013.01); *B01L 2300/0893* (2013.01); *C12Q 1/6869* (2013.01); *G01N 2021/6432* (2013.01); *G01N 2021/6441* (2013.01); *G01N 2021/6471* (2013.01); *G01N 2021/6478* (2013.01); *G01N 2021/6482* (2013.01); *G01N 21/76* (2013.01); *G01N 21/763* (2013.01); *G01N 2223/40* (2013.01); *G01N 2223/413* (2013.01); *G05B 2219/37563* (2013.01); *G16B 30/00* (2019.02)

(58) Field of Classification Search

None

See application file for complete search history.

(56) References Cited

U.S. PATENT DOCUMENTS

| | | | |
|---|---|---|---|
| 3,856,986 | A | 12/1974 | Macovski |
| 4,213,706 | A | 7/1980 | Hill et al. |
| 5,641,658 | A | 6/1997 | Adams et al. |
| 5,761,085 | A | 6/1998 | Giorgio |
| 6,090,592 | A | 7/2000 | Adams et al. |
| 6,188,478 | B1 | 2/2001 | Fuchs et al. |
| 6,641,658 | B1 | 11/2003 | Dubey |
| 6,898,004 | B2 | 5/2005 | Shimizu et al. |

(Continued)

FOREIGN PATENT DOCUMENTS

| | | | |
|---|---|---|---|
| CA | 2894317 | A1 | 12/2016 |
| CN | 1292227 | | 12/2006 |

(Continued)

OTHER PUBLICATIONS

Frohn et al., 2000, True optical resolution beyond the Rayleigh limit achieved by standing wave illumination PNAS, 97(13):7232-7236.

(Continued)

*Primary Examiner* — G. Steven Vanni

(74) *Attorney, Agent, or Firm* — Knobbe, Martens, Olson & Bear, LLP

(57) ABSTRACT

A device for base calling is provided. The device includes a receptacle configured to hold a biosensor having a sample surface holding a plurality of clusters during a sequence of sampling events, an array of sensors sensing information from clusters disposed in corresponding pixel areas of the sample surface during the sampling events and generate sequences of pixel signals and a communication port configured to output the sequences of pixel signals. The device also includes a signal processor coupled to the communication port and configured to receive and process at least one pixel signal in the sequences of pixel signals that mixes light gathered from at least two clusters in a corresponding pixel area, and to base call each of the at least two clusters using the at least one pixel signal.

20 Claims, 12 Drawing Sheets

(3 of 12 Drawing Sheet(s) Filed in Color)

(56) References Cited

U.S. PATENT DOCUMENTS

| | | | |
|---|---|---|---|
| 6,947,127 | B2 | 9/2005 | Wolleschensky et al. |
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,274,446 | B2 | 9/2007 | Wolleschensky et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,414,116 | B2 | 8/2008 | Milton et al. |
| 7,427,673 | B2 | 9/2008 | Balasubramanian et al. |
| 7,532,323 | B2 | 5/2009 | Tang et al. |
| 7,541,444 | B2 | 6/2009 | Milton et al. |
| 7,566,537 | B2 | 7/2009 | Balasubramanian et al. |
| 7,592,435 | B2 | 9/2009 | Milton et al. |
| 7,595,883 | B1 | 9/2009 | El Gamal et al. |
| 7,692,131 | B2 | 4/2010 | Fein et al. |
| 7,803,609 | B2 | 9/2010 | Kaplan |
| 8,160,379 | B2 | 4/2012 | Schafer et al. |
| 8,222,040 | B2 | 7/2012 | Hong et al. |
| 8,244,479 | B2 | 8/2012 | Kain et al. |
| 8,502,169 | B2 | 8/2013 | Rigneault et al. |
| 8,502,867 | B2 | 8/2013 | Park |
| 8,509,879 | B2 | 8/2013 | Durkin et al. |
| 8,759,077 | B2 | 6/2014 | Hong et al. |
| 8,796,185 | B2 | 8/2014 | Kim et al. |
| 8,817,362 | B2 | 8/2014 | Lee |
| 8,848,199 | B2 | 9/2014 | Choi et al. |
| 9,453,258 | B2 | 9/2016 | Kain et al. |
| 9,458,501 | B2 | 10/2016 | Hong et al. |
| 9,465,228 | B2 | 10/2016 | Lee et al. |
| 9,772,505 | B2 | 9/2017 | Lee et al. |
| 10,018,562 | B2 | 7/2018 | Lee et al. |
| 10,222,599 | B2 | 3/2019 | Ouchi et al. |
| 10,371,634 | B2 | 8/2019 | Rothberg et al. |
| 10,378,053 | B2 | 8/2019 | Staker et al. |
| 10,429,665 | B2 | 10/2019 | Lee et al. |
| 11,378,544 | B2 | 7/2022 | Dehlinger et al. |
| 11,561,196 | B2 | 1/2023 | Dehlinger et al. |
| 12,497,347 | B2 | 12/2025 | Dehlinger et al. |
| 2002/0055100 | A1 | 5/2002 | Kawashima et al. |
| 2003/0048819 | A1 | 3/2003 | Nagano et al. |
| 2004/0002090 | A1 | 1/2004 | Mayer et al. |
| 2004/0096853 | A1 | 5/2004 | Mayer |
| 2005/0100900 | A1 | 5/2005 | Kawashima et al. |
| 2005/0239113 | A1 | 10/2005 | Ryu et al. |
| 2005/0239115 | A1 | 10/2005 | Ryu et al. |
| 2006/0188901 | A1 | 8/2006 | Barnes et al. |
| 2006/0240439 | A1 | 10/2006 | Smith et al. |
| 2006/0281109 | A1 | 12/2006 | Barr Ost et al. |
| 2007/0046946 | A1 | 3/2007 | Namiki |
| 2007/0128624 | A1 | 6/2007 | Gormley et al. |
| 2007/0139541 | A1 | 6/2007 | Fein et al. |
| 2007/0166705 | A1 | 7/2007 | Milton et al. |
| 2008/0009420 | A1 | 1/2008 | Schroth et al. |
| 2008/0030628 | A1 | 2/2008 | Lundquist et al. |
| 2008/0108082 | A1 | 5/2008 | Rank et al. |
| 2008/0234136 | A1 | 9/2008 | Drmanac et al. |
| 2008/0242560 | A1 | 10/2008 | Gunderson et al. |
| 2009/0015831 | A1 | 1/2009 | Yguerabine et al. |
| 2009/0075838 | A1 | 3/2009 | El Gamal et al. |
| 2009/0127589 | A1 | 5/2009 | Rothberg et al. |
| 2009/0219607 | A1 | 9/2009 | Saggau et al. |
| 2009/0225407 | A1 | 9/2009 | Nakayama et al. |
| 2009/0238449 | A1 | 9/2009 | Zhang et al. |
| 2009/0250632 | A1 | 10/2009 | Kempe et al. |
| 2010/0141750 | A1 | 6/2010 | Osawa et al. |
| 2010/0296104 | A1 | 11/2010 | Abramovich et al. |
| 2011/0036996 | A1 | 2/2011 | Wolleschensky et al. |
| 2011/0059865 | A1 | 3/2011 | Smith et al. |
| 2012/0223214 | A1 | 9/2012 | Lee et al. |
| 2012/0256101 | A1 | 10/2012 | Ye et al. |
| 2012/0264132 | A1 | 10/2012 | Ismagilov et al. |
| 2013/0079232 | A1 | 3/2013 | Kain et al. |
| 2013/0110407 | A1 | 5/2013 | Baccash et al. |
| 2013/0210682 | A1 | 8/2013 | Eltoukhy et al. |
| 2013/0250407 | A1 | 9/2013 | Schaffer et al. |
| 2014/0001341 | A1 | 1/2014 | Hassibi et al. |
| 2014/0143188 | A1 | 5/2014 | Mackey et al. |
| 2014/0196550 | A1 | 7/2014 | Chernomorsky et al. |
| 2014/0274746 | A1 | 9/2014 | Khurana et al. |
| 2014/0320957 | A1 | 10/2014 | Ouchi et al. |
| 2015/0079596 | A1 | 3/2015 | Eltoukhy et al. |
| 2015/0093306 | A1 | 4/2015 | Thorne et al. |
| 2015/0213598 | A1 | 7/2015 | Madabhushi et al. |
| 2015/0266022 | A1 | 9/2015 | Eltoukhy et al. |
| 2015/0275289 | A1 | 10/2015 | Otwinowski et al. |
| 2015/0337388 | A1 | 11/2015 | Garner, Jr. et al. |
| 2016/0047749 | A1 | 2/2016 | Lee et al. |
| 2016/0124208 | A1 | 5/2016 | Best et al. |
| 2016/0273034 | A1 | 9/2016 | Lundquist et al. |
| 2016/0356715 | A1 | 12/2016 | Zhong et al. |
| 2017/0107562 | A1 | 4/2017 | Rothberg et al. |
| 2017/0145498 | A1 | 5/2017 | Saxena et al. |
| 2017/0349944 | A1 | 12/2017 | Rothberg et al. |
| 2018/0180547 | A1 | 6/2018 | Cao et al. |
| 2019/0012559 | A1 | 1/2019 | Desappan et al. |
| 2019/0212266 | A1 | 7/2019 | Baker |
| 2019/0212294 | A1 | 7/2019 | Dehlinger et al. |
| 2019/0284552 | A1 | 9/2019 | Collins et al. |
| 2020/0302297 | A1 | 9/2020 | Jaganathan et al. |
| 2020/0364496 | A1 | 11/2020 | Kostem |
| 2022/0299470 | A1 | 9/2022 | Dehlinger |
| 2023/0158494 | A1 | 5/2023 | Dehlinger et al. |

FOREIGN PATENT DOCUMENTS

| | | | |
|---|---|---|---|
| CN | 102449454 | A | 5/2012 |
| CN | 103534627 | A | 1/2014 |
| CN | 105043300 | A | 11/2015 |
| CN | 105980832 | A | 9/2016 |
| CN | 106471415 | A | 3/2017 |
| CN | 106770147 | A | 5/2017 |
| DE | 102016007839 | A1 | 12/2017 |
| JP | 2005-055219 | | 3/2005 |
| JP | 2005-080181 | | 3/2005 |
| JP | 2007199397 | A | 8/2007 |
| JP | 2013108626 | A | 6/2013 |
| JP | 2015501974 | A | 1/2015 |
| JP | 5900515 | B2 | 4/2016 |
| JP | 2017520821 | A | 7/2017 |
| JP | 2020524990 | A | 8/2020 |
| JP | 2020525760 | A | 8/2020 |
| KR | 20040001590 | | 1/2004 |
| KR | 20140081208 | A | 7/2014 |
| WO | 9106678 | A1 | 5/1991 |
| WO | 2004018497 | A2 | 3/2004 |
| WO | 2005065814 | A1 | 7/2005 |
| WO | 2006064199 | A1 | 6/2006 |
| WO | 2007010251 | A2 | 1/2007 |
| WO | 2007123744 | A2 | 11/2007 |
| WO | 2007135368 | A2 | 11/2007 |
| WO | 2008140758 | A1 | 11/2008 |
| WO | 2012031234 | A2 | 3/2012 |
| WO | WO 12/042967 | | 4/2012 |
| WO | 2012058096 | A1 | 5/2012 |
| WO | WO 12/118436 | | 9/2012 |
| WO | WO 13/035009 | | 3/2013 |
| WO | WO 13/070634 | | 5/2013 |
| WO | 2014144569 | A1 | 9/2014 |
| WO | WO 15/074005 | | 5/2015 |
| WO | 2015084985 | A2 | 6/2015 |
| WO | 2015089092 | A1 | 6/2015 |
| WO | 2015173222 | A1 | 11/2015 |
| WO | WO 16/023011 | | 2/2016 |
| WO | 2016061396 | A1 | 4/2016 |
| WO | WO 16/130704 | | 8/2016 |
| WO | 2016168996 | A1 | 10/2016 |
| WO | 2017045107 | A1 | 3/2017 |
| WO | 2017075428 | A1 | 5/2017 |
| WO | WO 17/153556 | | 9/2017 |
| WO | 2017184997 | A1 | 10/2017 |

(56) References Cited

FOREIGN PATENT DOCUMENTS

| | | | |
|---|---|---|---|
| WO | WO 17/214320 | | 12/2017 |
| WO | 2019136388 | A1 | 7/2019 |

OTHER PUBLICATIONS

Frohn et al., 2001, Three-dimensional resolution enhancement in fluorescence microscopy by harmonic excitation Optics Letters, 26(11):828-830.

Krishnamurthi et al., Apr. 10, 1996, Image processing in 3D standing-wave fluorescence microscopy Three-Dimensional Microscopy: Image Acquisition and Processing III vol. 2655, International Society for Optics and Photonics 18-25.

International Search Report and Written Opinion dated Apr. 10, 2019 in application No. PCT/US2019/012536.

Arpali, S. , "High-throughput screening of large volumes of whole blood using structured illumination and fluorescent on-chip imaging", Lab Chip, 12 (23), Sep. 12, 2012, 4968-4971.

Coskun, A. , et al., "Lensless wide-field fluorescent imaging on a chip using compressive decoding of sparse objects", Optics express, 18 (10), May 5, 2010, 10510-10523.

N2020621 , Search Report and Written Opinion mailed, Jan. 3, 2019, 12 pages.

Ilumina CMOS Chip and One-Channel SBS Chemistry, 2018, Illumina Inc, Tech Note (770-2013-054-B), 4 pages.

Ilumina CMOS Chip and One-Channel SBS Chemistry, Tech Note 2018 (770-2013-054-B), 4 pages.

Disposable Image Sensors: A revolution for microscopy & next-generation sequencing, Novus Light Today, Dec. 10, 2019, 2 pgs (retrieved from https://www.novuslight.com/disposable-image-sensors-a-revolution-for-microscopy-next-generation-sequencing_N9874.html Apr. 19, 2021).

James, JP Morgan—Illumina and iSeq, Enseqlopedia.com Jan. 2018, 3 pgs, (retrieved from http://enseqlopedia.com/2018/01/jp-morgan-illumina-iseq Apr. 2, 2021).

Fong, A comparison of next-generation sequencing protocols for microbial profiling, Massey Univ . . . Feb. 2015, 200 pgs.

Eraslan et al, Deep learning: new computational modelling techniques for genomics, Nature RevIeWS | GENETICs, vol. 20, Jul. 2019, pp. 389-403.

Angermueller et al., "Deep learning for computational biology", Molecular Systems Biology, vol. 12, No. 7, Jul. 1, 2016 (Jul. 1, 2016), p. 878, XP055540697, GB, ISSN: 1744-4292, DOI: 10.15252/msb.20156651.

KR 10-2019-7036425, First Office Action, dated Jan. 8, 2021, 5 pages.

Wang et. al., An adaptive decorrelation method removes Illumina DNA base-calling errors caused by crosstalk between adjacent clusters, Scientific Reports, published Feb. 20, 2017, 11 pages.

Giraud, Gerard, et. al."Fluorescence lifetime biosensing with DNA microarrays and a CMOSSPAD imager", 2010, 13 pages.

Illumina CMOS Chip and One-Channel SBS Chemistry, Illumina Inc, 2018, 4 pages.

Bentley et. al., Accurate Whole Human Genome Sequencing using Reversible Terminator Chemistry, Nature, Nov. 2008, 21 pages.

700A

| | AT Signal | CT Signal |
|---|---|---|
| **A** | 1 | 0 |
| **C** | 0 | 1 |
| **G** | 0 | 0 |
| **T** | 1 | 1 |

FIG. 7A

700B

Bright to Dim Cluster Intensity Ratio – 0.7:0.3

| Bins 701 | Bright Cluster 702 | Dim Cluster 704 | AT Signal 706 | CT Signal 708 (710) | AT Signal Portions 706A Bright Cluster | AT Signal Portions 706B Dim Cluster | CT Signal Portions 708A Bright Cluster | CT Signal Portions 708B Dim Cluster |
|---|---|---|---|---|---|---|---|---|
| Bin 1 | **A** | **A** | 1 | 0 | 0.7 | 0.3 | 0 | 0 |
| Bin 2 | **A** | **C** | 0.7 | 0.3 | 0.7 | 0 | 0 | 0.3 |
| Bin 3 | **A** | **G** | 0.7 | 0 | 0.7 | 0 | 0 | 0 |
| Bin 4 | **A** | **T** | 1 | 0.3 | 0.7 | 0.3 | 0 | 0.3 |
| Bin 5 | **C** | **A** | 0.3 | 0.7 | 0 | 0.3 | 0.7 | 0 |
| Bin 6 | **C** | **C** | 0 | 1 | 0 | 0 | 0.7 | 0.3 |
| Bin 7 | **C** | **G** | 0 | 0.7 | 0 | 0 | 0.7 | 0 |
| Bin 7 | **C** | **T** | 0.3 | 1 | 0 | 0.3 | 0.7 | 0.3 |
| Bin 9 | **G** | **A** | 0.3 | 0 | 0 | 0.3 | 0 | 0 |
| Bin 10 | **G** | **C** | 0 | 0.3 | 0 | 0 | 0 | 0.3 |
| Bin 11 | **G** | **G** | 0 | 0 | 0 | 0 | 0 | 0 |
| Bin 12 | **G** | **T** | 0.3 | 0.3 | 0 | 0.3 | 0 | 0.3 |
| Bin 13 | **T** | **A** | 1 | 0.7 | 0.7 | 0.3 | 0.7 | 0 |
| Bin 14 | **T** | **C** | 0.7 | 1 | 0.7 | 0 | 0.7 | 0.3 |
| Bin 15 | **T** | **G** | 0.7 | 0.7 | 0.7 | 0 | 0.7 | 0 |
| Bin 16 | **T** | **T** | 1 | 1 | 0.7 | 0.3 | 0.7 | 0.3 |

FIG. 7B

Off-Axis Illumination

SYSTEMS AND METHODS FOR DECODING PIXEL SIGNALS FOR BASE CALLING NUCLEIC ACIDS

PRIORITY APPLICATIONS

This application is a continuation of U.S. Nonprovisional application Ser. No. 17/831,424, titled "Semiconductor-Based Biosensors For Base Calling," filed Jun. 2, 2022 which is a continuation of U.S. Nonprovisional patent application Ser. No. 16/241,902, titled "High-Throughput Sequencing with Semiconductor-Based Detection," filed on Jan. 7, 2019, which in turn claims priority to or the benefit of the following applications:

U.S. Provisional Patent Application No. 62/614,930, entitled "High-Throughput Sequencing with Semiconductor-Based Detection," filed on Jan. 8, 2018; and U.S. Provisional Patent Application No. 62/614,934, titled "Systems and Devices For High-Throughput Sequencing with Semiconductor-Based Detection," filed on Jan. 8, 2018; and Netherlands Application No. 2020758, titled "High-Throughput Sequencing with Semiconductor-Based Detection," filed on Apr. 12, 2018.

The priority applications are hereby incorporated by reference for all purposes.

CROSS-REFERENCE TO OTHER APPLICATIONS

The following patent applications are incorporated herein in their entirety for all purposes:

U.S. Nonprovisional patent application No. 62/614,934, titled "Systems And Devices For High-Throughput Sequencing With Semiconductor-Based Detection," filed on Jan. 8, 2018 ;

U.S. Provisional patent application No. 62/614,690, titled "Multiplexing Of An Active Sensor Detector Using Structured Illumination," filed on Jan. 8, 2018;

U.S. Nonprovisional patent application Ser. No. 13/833,619, entitled "Biosensors For Biological Or Chemical Analysis And Systems And Methods For Same," filed on Mar. 15, 2013;

U.S. Nonprovisional patent application Ser. No. 15/175,489, titled "Biosensors For Biological Or Chemical Analysis And Methods Of Manufacturing The Same," filed on Jun. 7, 2016;

U.S. Nonprovisional patent application Ser. No. 13/882,088, titled "Microdevices And Biosensor Cartridges For Biological Or Chemical Analysis And Systems And Methods For The Same," filed on Apr. 26, 2013; and U.S. Nonprovisional patent application Ser. No. 13/624,200, titled "Methods And Compositions For Nucleic Acid Sequencing," filed on Sep. 21, 2012.

FIELD OF THE TECHNOLOGY DISCLOSED

Embodiments of the technology disclosed relate generally to sequencing with CMOS-based detection and more particularly to systems and methods for increasing throughput of sequencing with CMOS-based detection.

BACKGROUND

Various protocols in biological or chemical research involve performing a large number of controlled reactions on local support surfaces or within predefined reaction chambers (or wells). The desired reactions may then be observed or detected and subsequent analysis may help identify or reveal properties of chemicals involved in the reaction. For example, in some multiplex assays, an unknown analyte (e.g., clusters of clonally amplified nucleic acids) having an identifiable label (e.g., fluorescent label) may be exposed to thousands of known probes under controlled conditions. Each known probe may be deposited into a corresponding well of a microplate or flow cell. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing.

In some conventional fluorescent-detection protocols, an optical system is used to direct an excitation light onto fluorescently-labeled analytes and to also detect the fluorescent signals that may emit from the analytes. However, such optical systems can be relatively expensive and require a larger benchtop footprint. For example, the optical system may include an arrangement of lenses, filters, and light sources. In other proposed detection systems, the controlled reactions occur immediately over a solid-state imager (e.g., charged-coupled device (CCD) or a complementary metal-oxide-semiconductor (CMOS) sensor) that does not require a large optical assembly to detect the fluorescent emissions.

However, the proposed solid-state imaging systems may have some limitations. For example, the solid-state imagers are limited to one cluster base call per sensor (or pixel) and their throughput is dependent on the pixel density of the sensors, which is a function of the pixel pitch. Since there are limitations on significantly decreasing the pixel pitch, it becomes desirable to explore other solutions for increasing the throughput of solid-state imagers.

An opportunity arises to increase the throughput of solid-state imaging systems by base calling multiple clusters per sensor (or pixel) and to provide systems and devices that facilitate the multiple cluster base call per sensor (or pixel).

Embodiments of the present disclosure relate generally to biological or chemical analysis and more particularly to systems and methods using detection devices for biological or chemical analysis.

Various protocols in biological or chemical research involve performing a large number of controlled reactions on local support surfaces or within predefined reaction chambers. The desired reactions may then be observed or detected and subsequent analysis may help identify or reveal properties of chemicals involved in the reaction. For example, in some multiplex assays, unknown analytes having identifiable labels (e.g., fluorescent labels) may be exposed to thousands of known probes under controlled conditions. Each known probe may be deposited into a corresponding location on a surface. Observing any chemical reactions that occur between the known probes and the unknown analyte on the surface may help identify or reveal properties of the analyte. Other examples of such protocols include known DNA sequencing processes, such as sequencing-by-synthesis (SBS) or cyclic-array sequencing.

In some conventional fluorescent-detection protocols, an optical system is used to direct an excitation light onto fluorescently-labeled analytes and to also detect the fluorescent signals that may emit from the analytes. The throughput of standard imaging techniques is constrained by the number of pixels available in the detection device, among other things. As such, these optical systems can be relatively expensive and require a relatively large bench-top footprint when detecting surfaces having large collections of analytes. For example, nucleic acid arrays used in genotyping, expression, or sequencing analyses can require detection of millions of different sites on the array per square centimeter. Limits in throughput increase cost and decrease accuracy of these analyses.

Thus, there exists a need for higher throughput apparatus and methods, for example, to detect nucleic acid arrays. The present disclosure addresses this need and provides other advantages as well.

BRIEF DESCRIPTION OF THE TECHNOLOGY DISCLOSED

In accordance with one embodiment, a device for base calling is provided that comprises a receptacle configured to hold a biosensor. The biosensor has (a) a sample surface that holds a plurality of clusters during a sequence of sampling events, (b) an array of sensors configured to generate a plurality of sequences of pixel signals, and (c) a communication port which outputs the plurality of sequences of pixel signals. The array has a number N of active sensors and the sensors in the array are disposed relative to the sample surface to generate respective pixel signals during the sequence of sampling events from the number N of corresponding pixel areas of the sample surface to produce the plurality of sequences of pixel signals. The device further comprises a signal processor coupled to the receptacle. The signal processor is configured to receive and to process the plurality of sequences of pixel signals to classify results of the sequence of sampling events on clusters in the plurality of clusters, including using the plurality of sequences of pixel signals to classify results of the sequence of sampling events on a number N+M of clusters in the plurality of clusters from the number N of active sensors, where M is a positive integer.

The results of the sequence of sampling events can correspond to nucleotide bases in the clusters.

The sampling events can comprise two illumination stages in time sequence, and sequences of pixel signals in the plurality of sequences of pixel signals can include a set of signal samples for each sampling event, the set including at least one pixel signal from each of the two illumination stages.

The signal processor can include logic to classify results for two clusters from the sequences of pixel signals from a single sensor in the array of sensors. The logic to classify results for two clusters can include mapping a first pixel signal of the set of signal samples for a sampling event from a particular sensor into at least four bins, and mapping a second pixel signal of the set of signal samples for the sampling event into at least four bins, and logically combining the mapping of the first and second pixel signals to classify the results for two clusters.

The sensors in the array of sensors can comprise light detectors.

The sampling events can comprise two illumination stages in time sequence, and sequences of pixel signals in the plurality of sequences of pixel signals can include a set of signal samples for each sampling event, the set including at least one pixel signal from each of the two illumination stages. The first illumination stage can induce illumination from a given cluster indicating nucleotide bases A and T and the second illumination stage can induce illumination from a given cluster indicating nucleotide bases C and T, and said classifying results can comprise calling one of the nucleotide bases A, C, T or G.

Clusters can be distributed unevenly over the pixel areas of the sample surface, and the signal processor can execute time sequence and spatial analysis of the plurality of sequences of pixel signals to detect patterns of illumination corresponding to individual clusters on the sample surface, and to classify the results of the sampling events for the individual clusters. The plurality of sequences of pixel signals encodes differential crosstalk between at least two clusters resulting from their uneven distribution over the pixel areas.

The sample surface can comprise an array of wells overlying the pixel areas, including two wells per pixel area, the two wells per pixel area can include a dominant well and a subordinate well, the dominant well can have a larger cross section over the pixel area than the subordinate well.

The sample surface can comprise an array of wells overlying the pixel areas, and the sampling events can include at least one chemical stage with a number K of illumination stages where K is a positive integer. The illumination stages of the K illumination stages can illuminate the pixel areas with different angles of illumination, and the sequences of pixel signals can include a set of signal samples for each sampling event, the set including the number K of pixel signals for the at least one chemical stage of the sampling events.

The sample surface can comprise an array of wells overlying the pixel areas, and the sampling events can include a first chemical stage with a number K of illumination stages where K is a positive integer. The illumination stages of the K illumination stages can illuminate the pixel areas with different angles of illumination, and a second chemical stage with a number J of illumination stages where J is a positive integer. The illumination stages of the K illumination stages in the first chemical stage and of the J illumination stages in the second chemical stage can illuminate the wells in the array of wells with different angles of illumination, and the sequences of pixel signals can include a set of signal samples for each sampling event, the set including the number K of pixel signals for the first chemical stage plus the number J of pixel signals for the second chemical stage of the sampling events.

In another embodiment, a biosensor for base calling is provided. The biosensor comprises a sampling device. The sampling device includes a sample surface that has an array of pixel areas and a solid-state imager that has an array of sensors. Each sensor generates pixel signals in each base calling cycle. Each pixel signal represents light gathered from a corresponding pixel area of the sample surface. The biosensor further comprises a signal processor configured for connection to the sampling device. The signal processor receives and processes the pixel signals from the sensors for base calling in a base calling cycle, and uses the pixel signals from fewer sensors than a number of clusters base called in the base calling cycle.

A pixel area can receive light from a well on the sample surface and the well can hold more than one cluster during the base calling cycle.

A cluster can comprise a plurality of single-stranded deoxyribonucleic acid (abbreviated DNA) fragments that have an identical nucleic acid sequence.

In another embodiment, a method of base calling is provided. For a base calling cycle of a sequencing by synthesis (abbreviated SBS) run, the method includes detecting: (1) a first pixel signal that represents light gathered from a first pixel area during a first illumination stage of the base calling cycle and (2) a second pixel signal that represents light gathered from the first pixel area during a second illumination stage of the base calling cycle. The first pixel area underlies a plurality of clusters that shares the first pixel area. The method includes using a combination of the first and second pixel signals to identify nucleotide bases incorporated onto each cluster of the plurality of clusters during the base calling cycle.

The method can also include mapping the first pixel signal into at least four bins and mapping the second pixel signal into at least four bins, and combining the mapping of the first and second pixel signals to identify the incorporated nucleotide bases.

The method can also include applying the method to identify the nucleotide bases incorporated onto the plurality of clusters at a plurality of pixel areas during the base calling cycle.

The method can also include repeating the method over successive base calling cycles to identify the nucleotide bases incorporated onto the plurality of clusters at the plurality of pixel areas during each of the base calling cycles.

For each of the base calling cycles, the method can also include detecting and storing the first and second pixel signals emitted by the plurality of clusters at the plurality of pixel areas, and after the base calling cycles, using the combination of the first and second pixel signals to identify the nucleotide bases incorporated onto the plurality of clusters at the plurality of pixel areas during each of the previous base calling cycles.

The first pixel area can receive light from an associated well on a sample surface. The first pixel area can receive light from more than one associated well on the sample surface. The first and second pixel signals can be gathered by a first sensor from the first pixel area. The first and second pixel signals can be detected by a signal processor configured for processing pixel signals gathered by the first sensor. The first illumination stage can induce illumination from the first and second clusters to produce emissions from labeled nucleotide bases A and T and the second illumination stage can induce illumination from the first and second clusters to produce emissions from labeled nucleotide bases C and T.

In another embodiment, a method of identifying pixel areas with more than one cluster on a sample surface of a biosensor and base calling clusters at the identified pixel areas is provided. The method includes performing a plurality of base calling cycles, each base calling cycle having a first illumination stage and a second illumination stage. The method includes capturing at a sensor associated with a pixel area of the sample surface, (1) a first set of intensity values generated during the first illumination stage of the base calling cycles, and (2) a second set of intensity values generated during the second illumination stage of the base calling cycles. The method includes fitting sixteen distributions to the first and second sets of intensity values using a signal processor and, based on the fitting, classifying the pixel area as having more than one cluster. For a successive base calling cycle, the method includes detecting the first and second sets of intensity values for a cluster group at the pixel area using the signal processor, and selecting a distribution for the cluster group. The distribution identifies a nucleotide base present in each cluster of the cluster group.

The method can include fitting comprises using one or more algorithms, including a k-means clustering algorithm, a k-means-like clustering algorithm, an expectation maximization algorithm, and a histogram based algorithm.

The method can include normalizing the intensity values.

The pixel area can receive light from an associated well on the sample surface.

In another embodiment, a device for base calling is provided. The device comprises a receptacle configured to hold a biosensor. The biosensor has a sample surface. The sample surface includes pixel areas that underlay a plurality of clusters during a sequence of sampling events such that the clusters are distributed unevenly over the pixel areas. The biosensor also has an array of sensors configured to generate a plurality of sequences of pixel signals. The array has a number N of active sensors. The sensors in the array are disposed relative to the sample surface to generate respective pixel signals during the sequence of sampling events from the number N of corresponding pixel areas of the sample surface to produce the plurality of sequences of pixel signals. The biosensor also has a communication port which outputs the plurality of sequences of pixel signals. The device further comprises a signal processor coupled to the receptacle. The signal processor is configured to execute time sequence and spatial analysis of the plurality of sequences of pixel signals to detect patterns of illumination corresponding to a number N+M of individual clusters on the sample surface from the number N of active sensors, where M is a positive integer, and to classify the results of the sequence of sampling events for the number N+M of individual clusters. The plurality of sequences of pixel signals encodes differential crosstalk between at least two clusters resulting from their uneven distribution over the pixel areas.

The signal processor can use the detected patterns of illumination to locate the number N+M of individual clusters on the sample surface from the number N of active sensors.

In another embodiment, a device for base calling is provided. The device comprises a biosensor. The biosensor has a sample surface. The sample surface includes pixel areas and an array of wells overlying the pixel areas, including two wells per pixel area. The two wells per pixel area include a dominant well and a subordinate well. The dominant well has a larger cross section over the pixel area than the subordinate well.

The two wells can have different offsets relative to a center of the pixel area. During a sampling event, the pixel area can receive different amounts of illumination from the two wells. Each of the two wells can hold at least one cluster during the sampling event. During the sampling event, the pixel area can receive an amount of illumination from a bright cluster in the dominant well that is greater than an amount of illumination received from a dim cluster in the subordinate well.

The biosensor can be coupled to a signal processor. The signal processor can be configured to receive and to process the plurality of sequences of pixel signals to identify nucleotide bases present in a number N+M of clusters from the number N of active sensors. For the bright and dim cluster, this can include mapping into at least four bins a first pixel signal generated by a sensor corresponding to the pixel area during a first illumination stage of the sampling event, mapping into at least four bins a second pixel signal generated by the sensor during a second illumination stage of the sampling event, and logically combining the mapping of the first and second pixel signals to identify the nucleotide bases present in the bright cluster and the dim cluster.

The biosensor also has an array of sensors configured to generate a plurality of sequences of pixel signals. The array has a number N of active sensors. The sensors in the array are disposed relative to the sample surface to generate respective pixel signals during the sequence of sampling events from the number N of corresponding pixel areas of the sample surface to produce the plurality of sequences of pixel signals. The biosensor also has a communication port which outputs the plurality of sequences of pixel signals.

In yet another embodiment, a device for base calling is provided. The device comprises a biosensor. The biosensor has a sample surface. The sample surface includes pixel areas and an array of wells overlying the pixel areas. The device further comprises an illumination system. The illumination system illuminates the pixel areas with different angles of illumination during a sequence of sampling events, including for a sampling event in the sequence of sampling events illuminating each of the wells with off-axis illumination to produce asymmetrically illuminated well regions in each of the wells.

The asymmetrically illuminated regions of a well can include at least a dominant well region and a subordinate well region, such that during the sampling event the dominant well region is illuminated more than the subordinate well region. The well can hold more than one cluster during the sampling event, with the dominant and subordinate well regions each including a cluster. During the sampling event, a pixel area overlying the well can receive an amount of illumination from a bright cluster in the dominant well region that is greater than an amount of illumination received from a dim cluster in the subordinate well region.

The off-axis illumination can be at a forty-five degree angle. In some embodiments, one well overlies per pixel area. In other embodiments, two wells overlie per pixel area.

The biosensor can be coupled to a signal processor. The signal processor can be configured to receive and to process the plurality of sequences of pixel signals to identify nucleotide bases present in a number N+M of clusters from the number N of active sensors. For the bright and dim cluster, this can include mapping into at least four bins a first pixel signal generated by a sensor corresponding to the pixel area during a first illumination stage of the sampling event, mapping into at least four bins a second pixel signal generated by the sensor during a second illumination stage of the sampling event, and logically combining the mapping of the first and second pixel signals to identify the nucleotide bases present in the bright cluster and the dim cluster.

The biosensor also has an array of sensors configured to generate a plurality of sequences of pixel signals. The array has a number N of active sensors. The sensors in the array are disposed relative to the sample surface to generate respective pixel signals during the sequence of sampling events from the number N of corresponding pixel areas of the sample surface to produce the plurality of sequences of pixel signals. The biosensor also has a communication port which outputs the plurality of sequences of pixel signals.

In accordance with another embodiment, a device for base calling is provided that comprises a receptacle configured to hold a biosensor. The biosensor has (a) a sample surface that holds a plurality of clusters during a sequence of sampling events, (b) an array of sensors configured to generate a plurality of sequences of pixel signals, and (c) a communication port which outputs the plurality of sequences of pixel signals. Each sensor in the array senses information from one or more clusters disposed in corresponding pixel areas of the sample surface to generate a pixel signal in a sampling event. The array has a number N of active sensors and the sensors in the array are disposed relative to the sample surface to generate respective pixel signals during the sequence of sampling events from the number N of corresponding pixel areas of the sample surface to produce the plurality of sequences of pixel signals. The device further comprises a signal processor coupled to the receptacle. The signal processor is configured to receive and to process the plurality of sequences of pixel signals to classify results of the sequence of sampling events on clusters in the plurality of clusters. The pixel signal for each sampling event in at least one sequence of pixel signals in the plurality of sequences of pixel signals represents sensed information from at least two clusters in the corresponding pixel area. The signal processor uses the plurality of sequences of pixel signals to classify results of the sequence of sampling events on a number N+M of clusters in the plurality of clusters from the number N of active sensors, where M is a positive integer.

The results of the sequence of sampling events can correspond to nucleotide bases in the clusters.

The sampling events can comprise two illumination stages in time sequence, and said at least one sequence of pixel signals in the plurality of sequences of pixel signals can include one pixel signal including information from at least two clusters in the corresponding pixel area from each of the two illumination stages.

The signal processor can include logic to classify results for two clusters from the sequences of pixel signals from said at least one sequence of pixel signals. The logic to classify results for two clusters can include mapping a first pixel signal in said at least one sequence of pixel signals from a particular sensor into at least four bins, and mapping a second pixel signal in said at least one sequence of pixel signals into at least four bins, and logically combining the mapping of the first and second pixel signals to classify the results for two clusters.

The sensors in the array of sensors can comprise light detectors.

The sampling events can comprise two illumination stages in time sequence, and sequences of pixel signals in the plurality of sequences of pixel signals include at least one pixel signal from each of the two illumination stages. The first illumination stage can induce illumination from one or more clusters in the pixel areas of the sensors indicating nucleotide bases A and T and the second illumination stage induces illumination from one or more clusters in the pixel areas of the sensors indicating nucleotide bases C and T, and said classifying results comprises calling one of the nucleotide bases A, C, T or G for at least two clusters using said at least one sequence.

Clusters can be distributed unevenly over the pixel areas of the sample surface, and the signal processor can execute time sequence and spatial analysis of the plurality of sequences of pixel signals to detect patterns of illumination corresponding to individual clusters on the sample surface, and to classify the results of the sampling events for the individual clusters. The plurality of sequences of pixel signals encodes differential crosstalk between at least two clusters resulting from their uneven distribution over the pixel areas.

The sample surface can comprise an array of wells overlying the pixel areas, including two wells per pixel area, the two wells per pixel area can include a dominant well and a subordinate well, the dominant well can have a larger cross section over the pixel area than the subordinate well.

The sample surface can comprise an array of wells overlying the pixel areas, and the sampling events can include at least one chemical stage with a number K of illumination stages where K is a positive integer. The illumination stages of the K illumination stages can illuminate the pixel areas with different angles of illumination, and the sequences of pixel signals can include the number K of pixel signals for the at least one chemical stage of the sampling events.

The sample surface can comprise an array of wells overlying the pixel areas, and the sampling events can include a first chemical stage with a number K of illumination stages where K is a positive integer. The illumination stages of the K illumination stages can illuminate the pixel areas with different angles of illumination, and a second chemical stage with a number J of illumination stages where J is a positive integer. The illumination stages of the K illumination stages in the first chemical stage and of the J illumination stages in the second chemical stage can illuminate the wells in the array of wells with different angles of illumination, and the sequences of pixel signals can include the number K of pixel signals for the first chemical stage plus the number J of pixel signals for the second chemical stage of the sampling events.

In yet another embodiment, a biosensor for base calling is provided. The biosensor comprises a sampling device. The sampling device includes a sample surface that has an array of pixel areas and a solid-state imager that has an array of sensors. Each sensor generates pixel signals in each base calling cycle. Each pixel signal represents light gathered in one base calling cycle from one or more clusters in a corresponding pixel area of the sample surface. The biosensor further comprises a signal processor configured for connection to the sampling device. The signal processor receives and processes the pixel signals from the sensors for base calling in a base calling cycle, and uses the pixel signals from fewer sensors than a number of clusters base called in the base calling cycle. The pixel signals from the fewer sensors include at least one pixel signal representing light gathered from at least two clusters in the corresponding pixel area.

A pixel area can receive light from a well on the sample surface and the well can hold more than one cluster during the base calling cycle.

A cluster can comprise a plurality of single-stranded fragments that have an identical base sequence.

In a further embodiment, a method of base calling is provided. For a base calling cycle of a sequencing by synthesis (abbreviated SBS) run, the method includes detecting: (1) a first pixel signal that represents light gathered from at least two clusters in a first pixel area during a first illumination stage of the base calling cycle and (2) a second pixel signal that represents light gathered from said at least two clusters in the first pixel area during a second illumination stage of the base calling cycle. The first pixel area underlies a plurality of clusters that shares the first pixel area. The method includes using a combination of the first and second pixel signals to identify nucleotide bases incorporated onto each cluster of the at least two clusters during the base calling cycle.

The method can also include mapping the first pixel signal into at least four bins and mapping the second pixel signal into at least four bins, and combining the mapping of the first and second pixel signals to identify the incorporated nucleotide bases.

The method can also include applying the method to identify the nucleotide bases incorporated onto the plurality of clusters at a plurality of pixel areas during the base calling cycle.

The method can also include repeating the method over successive base calling cycles to identify the nucleotide bases incorporated onto the plurality of clusters at the plurality of pixel areas during each of the base calling cycles.

For each of the base calling cycles, the method can also include detecting and storing the first and second pixel signals emitted by the plurality of clusters at the plurality of pixel areas, and after the base calling cycles, using the combination of the first and second pixel signals to identify the nucleotide bases incorporated onto the plurality of clusters at the plurality of pixel areas during each of the previous base calling cycles.

The first pixel area can receive light from an associated well on a sample surface. The first pixel area can receive light from more than one associated well on the sample surface. The first and second pixel signals can be gathered by a first sensor from the first pixel area. The first and second pixel signals can be detected by a signal processor configured for processing pixel signals gathered by the first sensor. The first illumination stage can induce illumination from the first and second clusters to produce emissions from labeled nucleotide bases A and T and the second illumination stage can induce illumination from the first and second clusters to produce emissions from labeled nucleotide bases C and T.

In another embodiment, a method of identifying pixel areas with more than one cluster on a sample surface of a biosensor and base calling clusters at the identified pixel areas is provided. The method includes performing a plurality of base calling cycles, each base calling cycle having a first illumination stage and a second illumination stage. The method includes capturing at a sensor associated with a pixel area of the sample surface, (1) a first set of intensity values generated during the first illumination stage of the base calling cycles, and (2) a second set of intensity values generated during the second illumination stage of the base calling cycles. The method includes fitting the first and second sets of intensity values to a set of distributions using a signal processor and, based on the fitting, classifying the pixel area as having more than one cluster. For a successive base calling cycle, the method includes detecting the first and second sets of intensity values for a cluster group at the pixel area using the signal processor, and selecting a distribution for the cluster group. The distribution identifies a nucleotide base present in each cluster of the cluster group.

The method can include fitting comprises using one or more algorithms, including a k-means clustering algorithm, a k-means-like clustering algorithm, an expectation maximization algorithm, and a histogram based algorithm.

The method can include normalizing the intensity values.

The pixel area can receive light from an associated well on the sample surface.

In another embodiment, a device for base calling is provided. The device comprises a receptacle configured to hold a biosensor. The biosensor has a sample surface. The sample surface includes pixel areas that underlay a plurality of clusters during a sequence of sampling events such that the clusters are distributed unevenly over the pixel areas. The biosensor also has an array of sensors configured to generate a plurality of sequences of pixel signals. Each sensor in the array senses information from one or more clusters disposed in corresponding pixel areas of the sample surface to generate a pixel signal in a sampling event. The array has a number N of active sensors. The sensors in the array are disposed relative to the sample surface to generate respective pixel signals during the sequence of sampling events from the number N of corresponding pixel areas of the sample surface to produce the plurality of sequences of pixel signals. The biosensor also has a communication port which outputs the plurality of sequences of pixel signals. The device further comprises a signal processor coupled to the receptacle. The signal processor is configured to execute time sequence and spatial analysis of the plurality of sequences of pixel signals to detect patterns of illumination corresponding to a number N+M of individual clusters on the sample surface from the number N of active sensors, where M is a positive integer, and to classify the results of the sequence of sampling events for the number N+M of individual clusters. The pixel signal for each sampling event in at least one sequence of pixel signals in the plurality of sequences of pixel signals represents sensed information from at least two clusters in the corresponding pixel area and the plurality of sequences of pixel signals encodes differential crosstalk between the at least two clusters resulting from their uneven distribution over the pixel areas.

The signal processor can use the detected patterns of illumination to locate the number N+M of individual clusters on the sample surface from the number N of active sensors.

In another embodiment, a device for base calling is provided. The device comprises a biosensor. The biosensor has a sample surface. The sample surface includes pixel areas and an array of wells overlying the pixel areas, the biosensor including two wells and two clusters per pixel area. The two wells per pixel area include a dominant well and a subordinate well. The dominant well has a larger cross section over the pixel area than the subordinate well.

The biosensor also has an array of sensors configured to generate a plurality of sequences of pixel signals. Each sensor in the array senses information from the two clusters disposed in corresponding pixel areas of the sample surface to generate a pixel signal in a sampling event. The array has a number N of active sensors. The sensors in the array are disposed relative to the sample surface to generate respective pixel signals during the sequence of sampling events from the number N of corresponding pixel areas of the sample surface to produce the plurality of sequences of pixel signals. The biosensor also has a communication port which outputs the plurality of sequences of pixel signals.

The two wells can have different offsets relative to a center of the pixel area. During a sampling event, the pixel area can receive different amounts of illumination from the two wells. The pixel signal for each sampling event in at least one sequence of pixel signals in the plurality of sequences of pixel signals represents sensed information from the two clusters in the corresponding pixel area. Each of the two wells can hold at least one cluster during the sampling event. During the sampling event, the pixel area can receive an amount of illumination from a bright cluster in the dominant well that is greater than an amount of illumination received from a dim cluster in the subordinate well.

The biosensor can be coupled to a signal processor. The signal processor can be configured to receive and to process the plurality of sequences of pixel signals to identify nucleotide bases present in a number N+M of clusters from the number N of active sensors. For the bright and dim cluster, this can include mapping into at least four bins a first pixel signal generated by a sensor corresponding to the pixel area during a first illumination stage of the sampling event, mapping into at least four bins a second pixel signal generated by the sensor during a second illumination stage of the sampling event, and logically combining the mapping of the first and second pixel signals to identify the nucleotide bases present in the bright cluster and the dim cluster.

In yet another embodiment, a device for base calling is provided. The device comprises a biosensor. The biosensor has a sample surface. The sample surface includes pixel areas and an array of wells overlying the pixel areas, with at least two clusters per pixel area. The device further comprises an illumination system. The illumination system illuminates the pixel areas with different angles of illumination during a sequence of sampling events, including for a sampling event in the sequence of sampling events illuminating each of the wells with off-axis illumination to produce asymmetrically illuminated well regions in each of the wells.

The asymmetrically illuminated regions of a well can include at least a dominant well region and a subordinate well region, such that during the sampling event the dominant well region is illuminated more than the subordinate well region. The well can hold more than one cluster during the sampling event, with the dominant and subordinate well regions each including a cluster. During the sampling event, a pixel area overlying the well can receive an amount of illumination from a bright cluster in the dominant well region that is greater than an amount of illumination received from a dim cluster in the subordinate well region.

The off-axis illumination can be at a forty-five degree angle. In some embodiments, one well overlies per pixel area. In other embodiments, two wells overlie per pixel area.

The biosensor also has an array of sensors configured to generate a plurality of sequences of pixel signals. Each sensor in the array senses information from the at least two clusters disposed in corresponding pixel areas of the sample surface to generate a pixel signal in a sampling event. The array has a number N of active sensors. The sensors in the array are disposed relative to the sample surface to generate respective pixel signals during the sequence of sampling events from the number N of corresponding pixel areas of the sample surface to produce the plurality of sequences of pixel signals. The biosensor also has a communication port which outputs the plurality of sequences of pixel signals.

The biosensor can be coupled to a signal processor. The signal processor can be configured to receive and to process the plurality of sequences of pixel signals to identify nucleotide bases present in a number N+M of clusters from the number N of active sensors. For the bright and dim cluster, this can include mapping into at least four bins a first pixel signal generated by a sensor corresponding to the pixel area during a first illumination stage of the sampling event, mapping into at least four bins a second pixel signal generated by the sensor during a second illumination stage of the sampling event, and logically combining the mapping of the first and second pixel signals to identify the nucleotide bases present in the bright cluster and the dim cluster.

Other features and aspects of the technology disclosed will become apparent from the following detailed description, taken in conjunction with the accompanying drawings, which illustrate, by way of example, the features in accordance with embodiments of the technology disclosed. This brief description is not intended to limit the scope of any inventions described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The color drawings also may be available in PAIR via the Supplemental Content tab. The present disclosure, in accordance with one or more embodiments, is described in detail with reference to the following figures. The figures are provided for purposes of illustration only and merely depict example embodiments. Furthermore, it should be noted that for clarity and ease of illustration, the elements in the figures have not necessarily been drawn to scale.

Some of the figures included herein illustrate various embodiments of the technology disclosed from different viewing angles. Although the accompanying descriptive text may refer to such views as "top," "bottom" or "side" views, such references are merely descriptive and do not imply or require that the technology disclosed be implemented or used in a particular spatial orientation unless explicitly stated otherwise.

Figure 1:
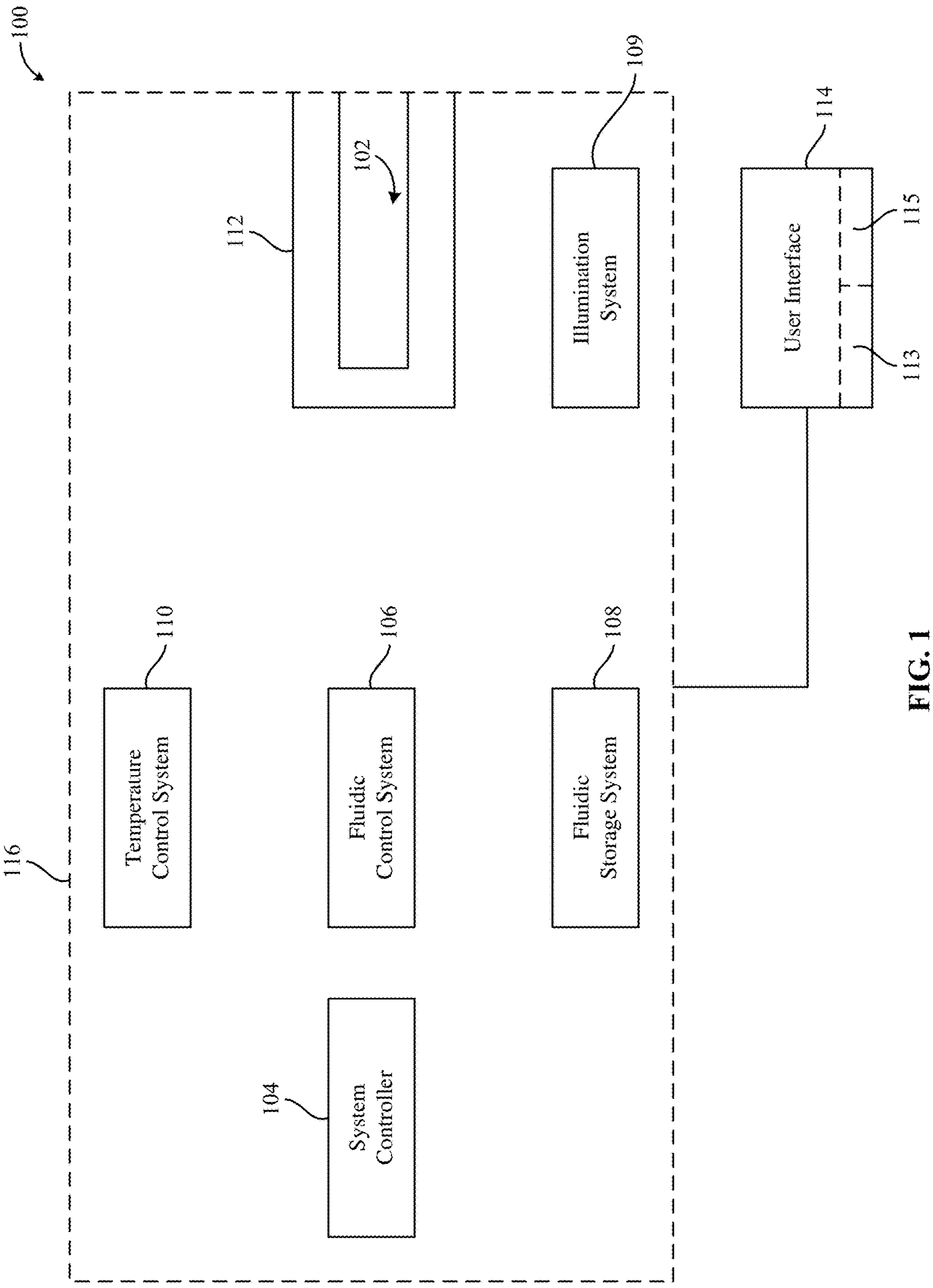

FIG. 1 is a block diagram of a base calling system in accordance with one embodiment.

Figure 2:
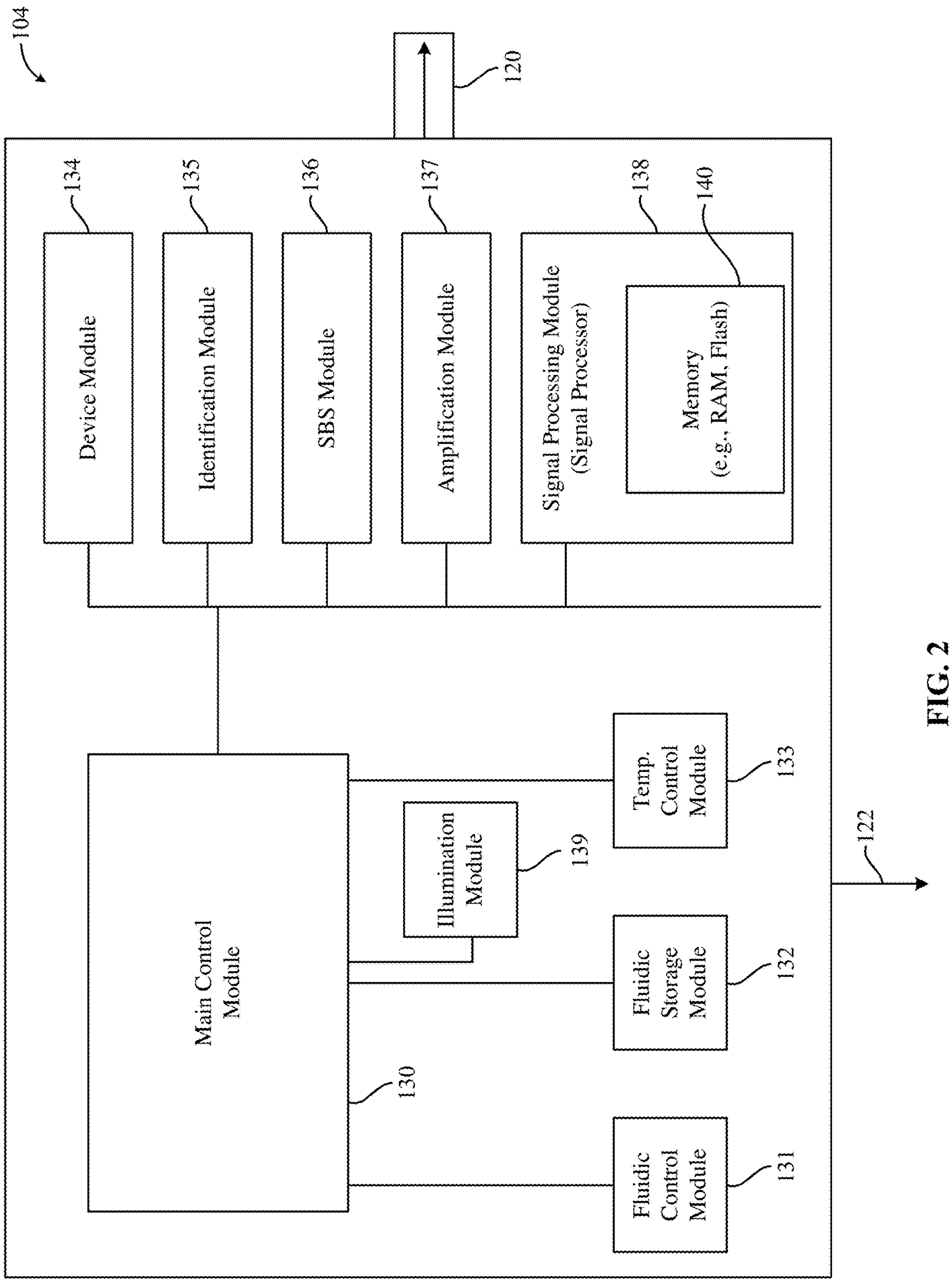

FIG. 2 is a block diagram of a system controller that can be used in the system of FIG. 1.

Figure 3:
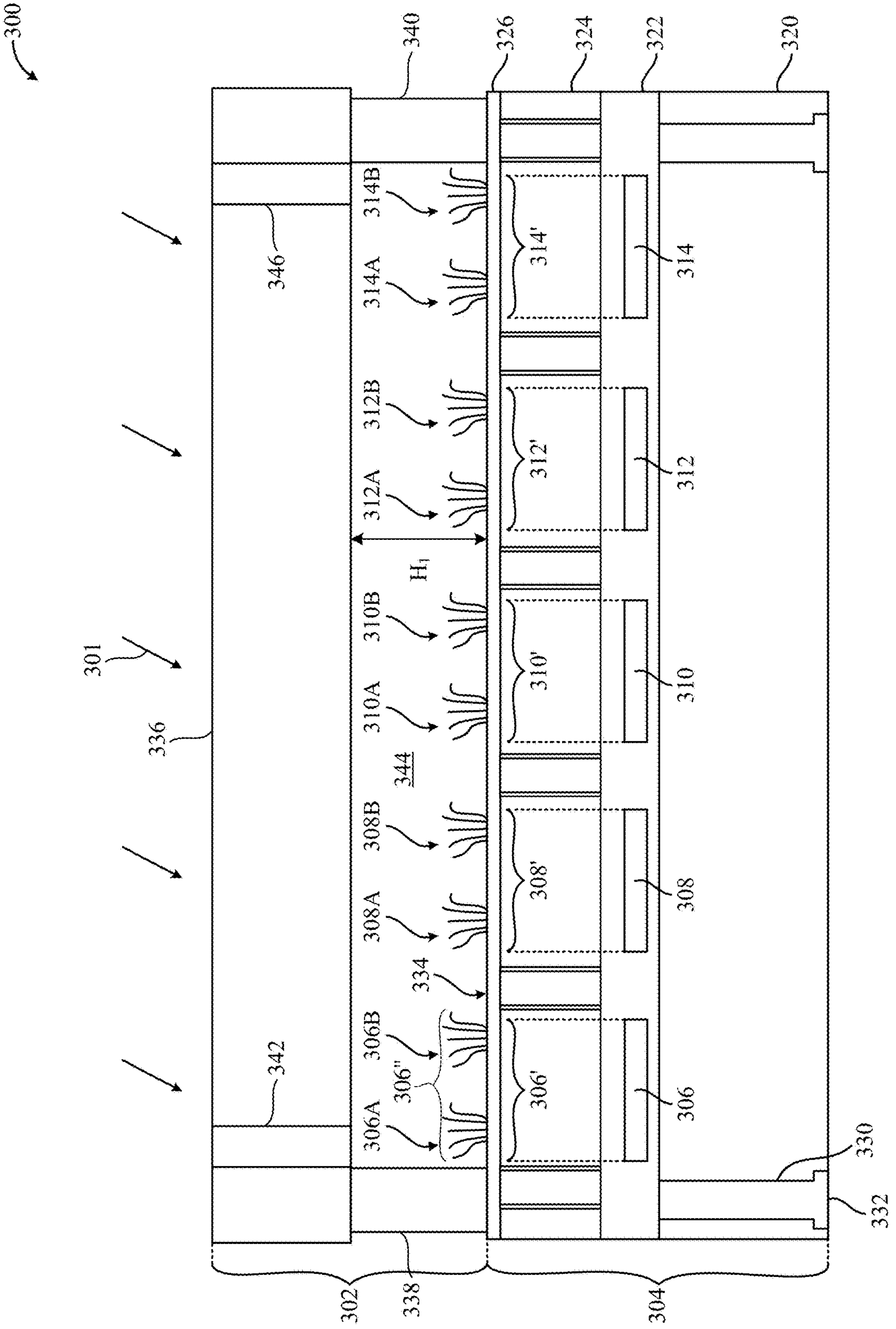

FIG. 3 illustrates a cross-section of a biosensor that can be used in various embodiments. FIG. 3's biosensor has pixel areas that can each hold more than one cluster during a base calling cycle (e.g., 2 clusters per pixel area).

Figure 4:
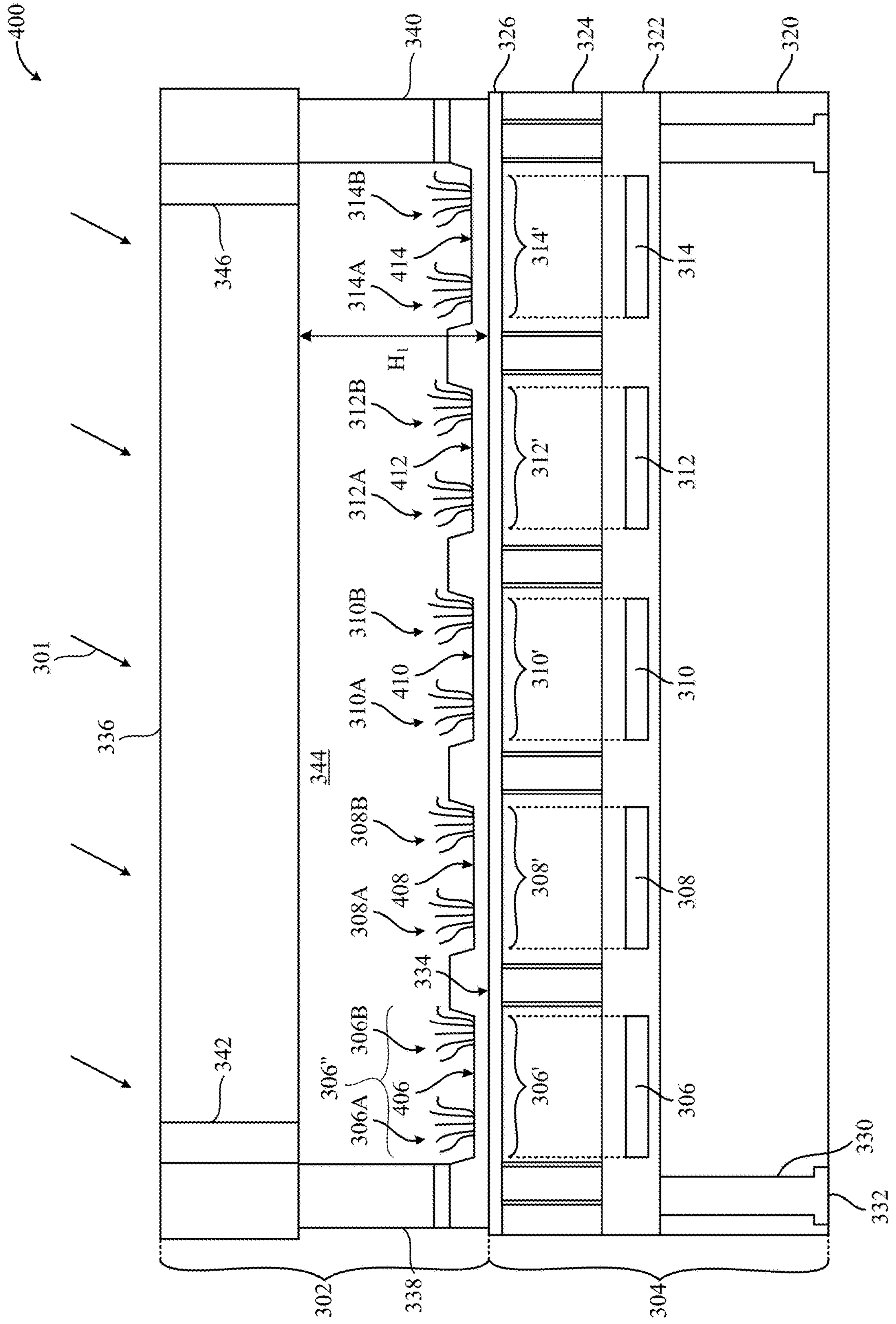

FIG. 4 shows a cross-section of a biosensor that can be used in various embodiments. FIG. 4's biosensor has wells that can each hold more than one cluster during a base calling cycle (e.g., 2 clusters per well).

Figure 5A:
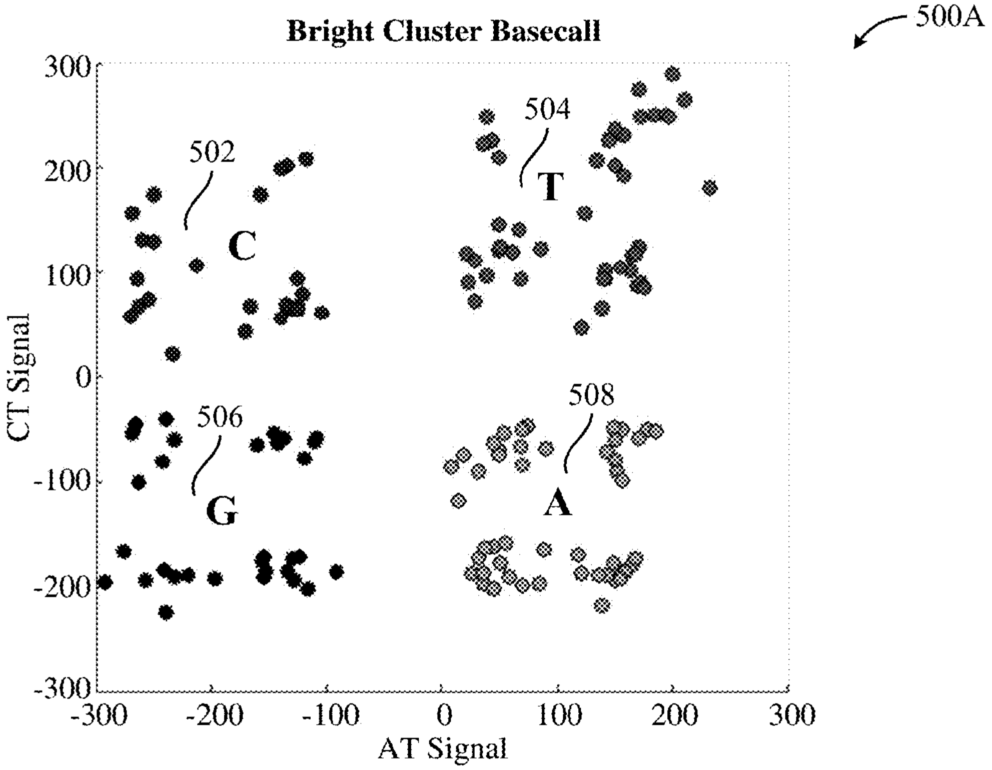
Figure 5B:
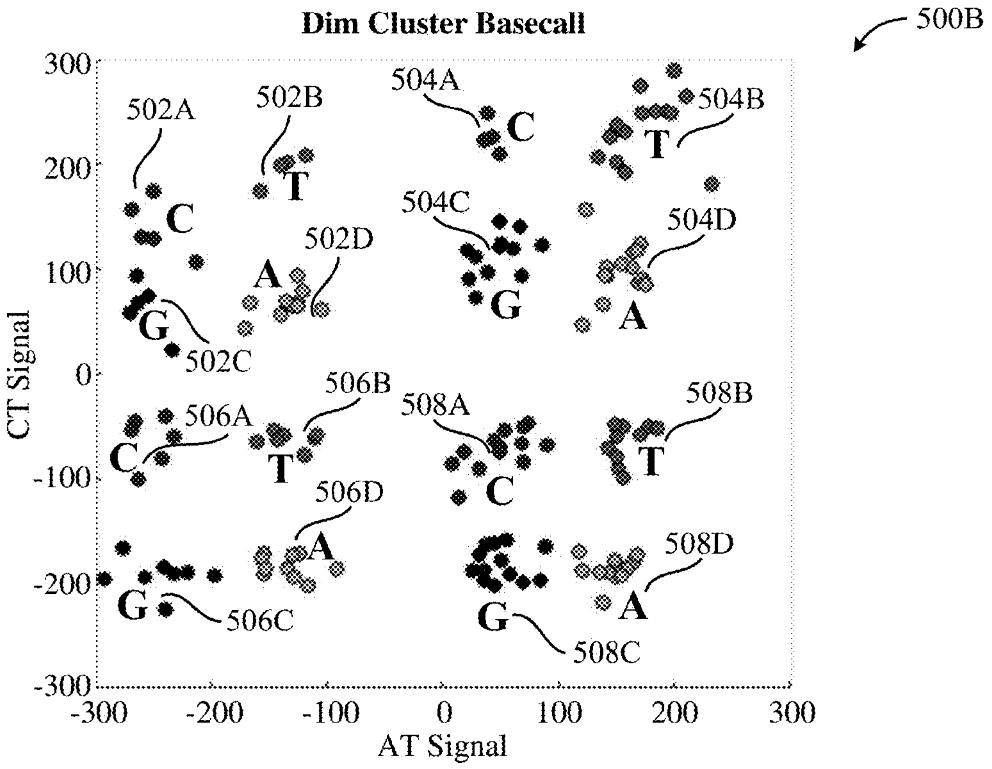

FIGS. 5A and 5B are scatter plots that depict base calling of bright and dim clusters of a cluster pair using their respective pixel signals detected by a shared sensor (or pixel) in accordance with one embodiment.

Figure 6:
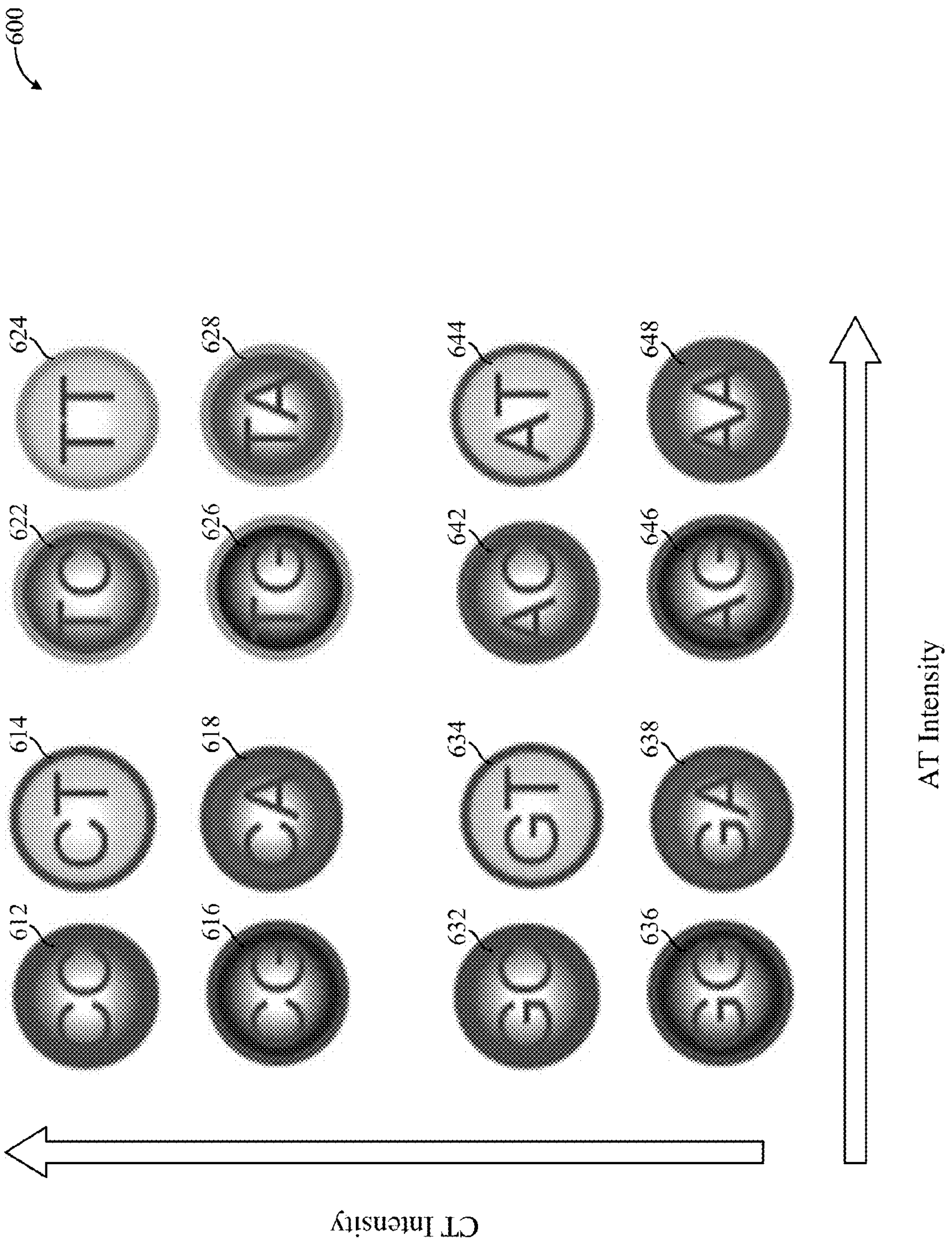

FIG. 6 is a scatter plot that depicts sixteen distributions produced by intensity values from bright and dim clusters of a cluster pair in accordance with one embodiment.

FIG. 7A is a detection table that illustrates a base calling scheme for one dye and two illumination stage sequencing protocol in accordance with one embodiment.

FIG. 7B is a base calling table that shows a classification scheme for classifying combined pixel signals from bright and dim clusters of a cluster pair into one of sixteen bins in accordance with one embodiment.

Figure 8:
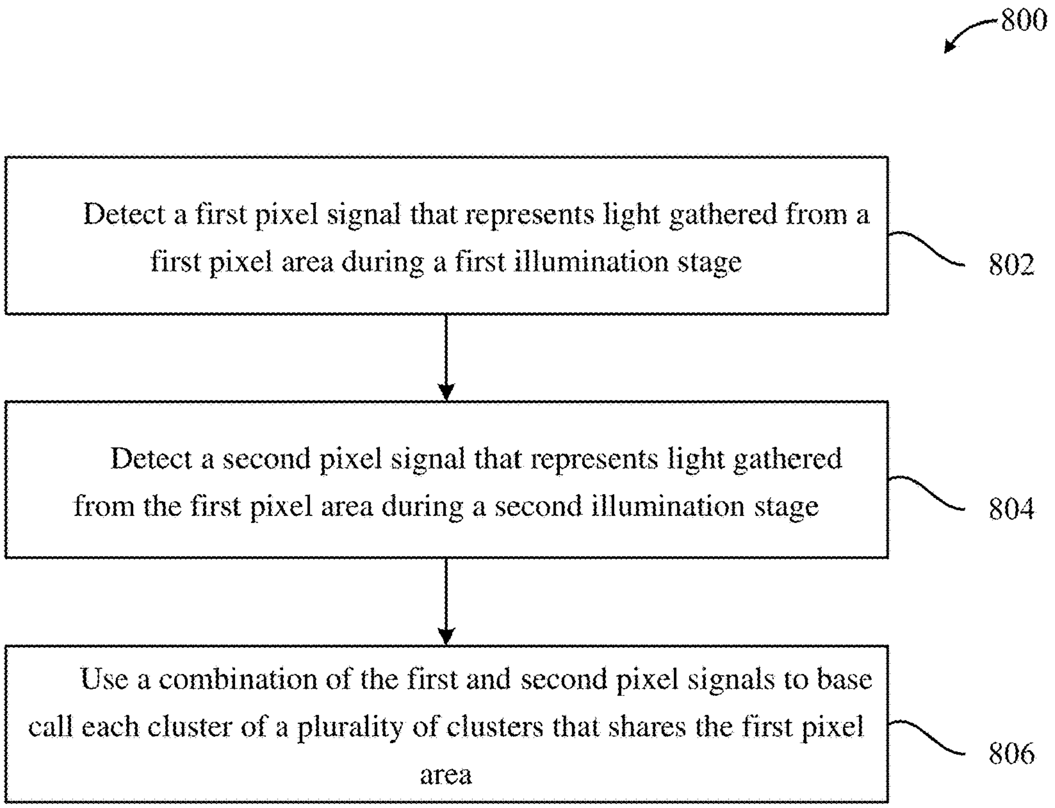

FIG. 8 shows a method of base calling by analyzing pixel signals emitted by a plurality of clusters that share a pixel area in accordance with one embodiment.

Figure 9:
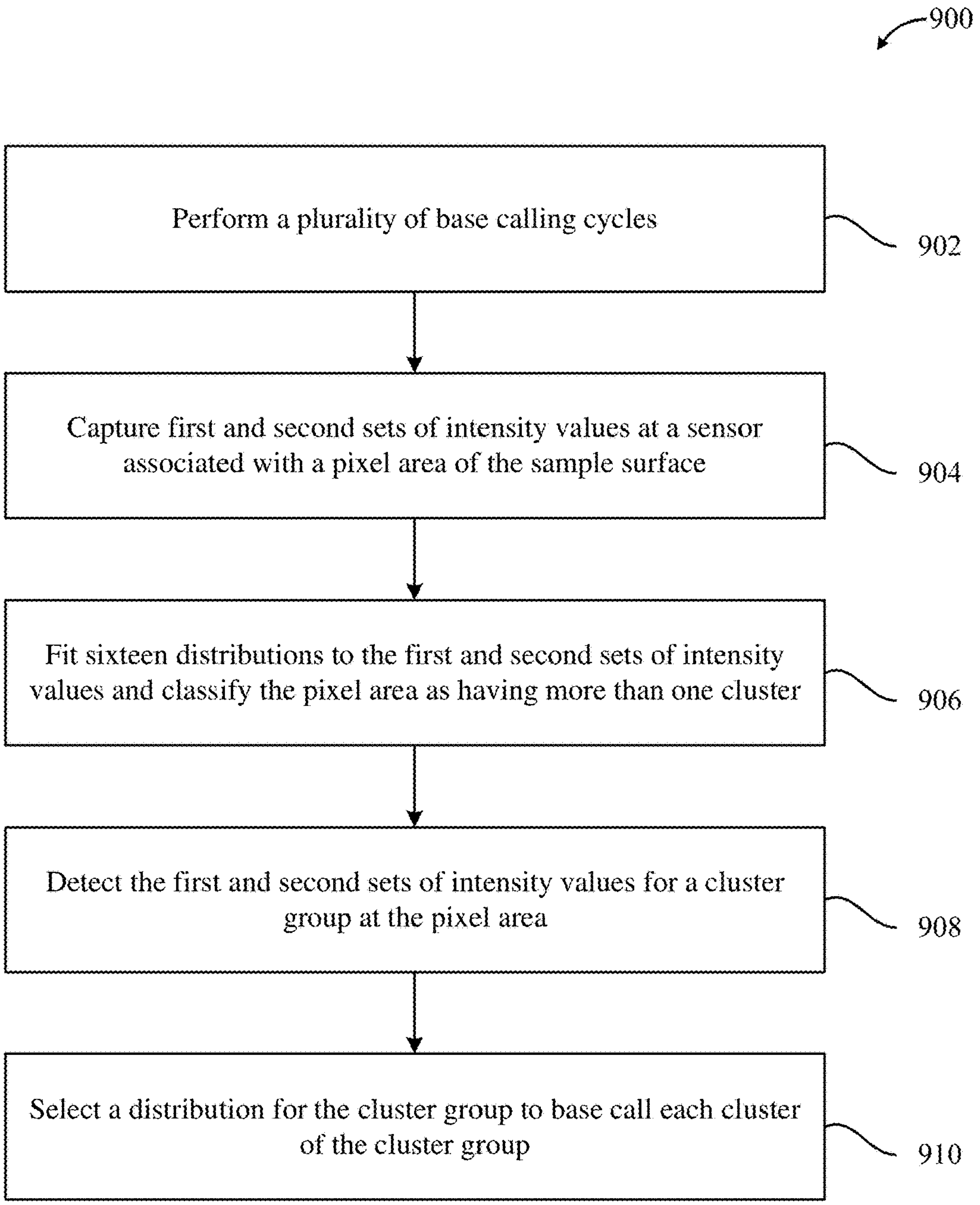

FIG. 9 depicts a method of identifying pixel areas with more than one cluster on a sample surface of a biosensor and base calling clusters at the identified pixel areas in accordance with one embodiment.

Figure 10:
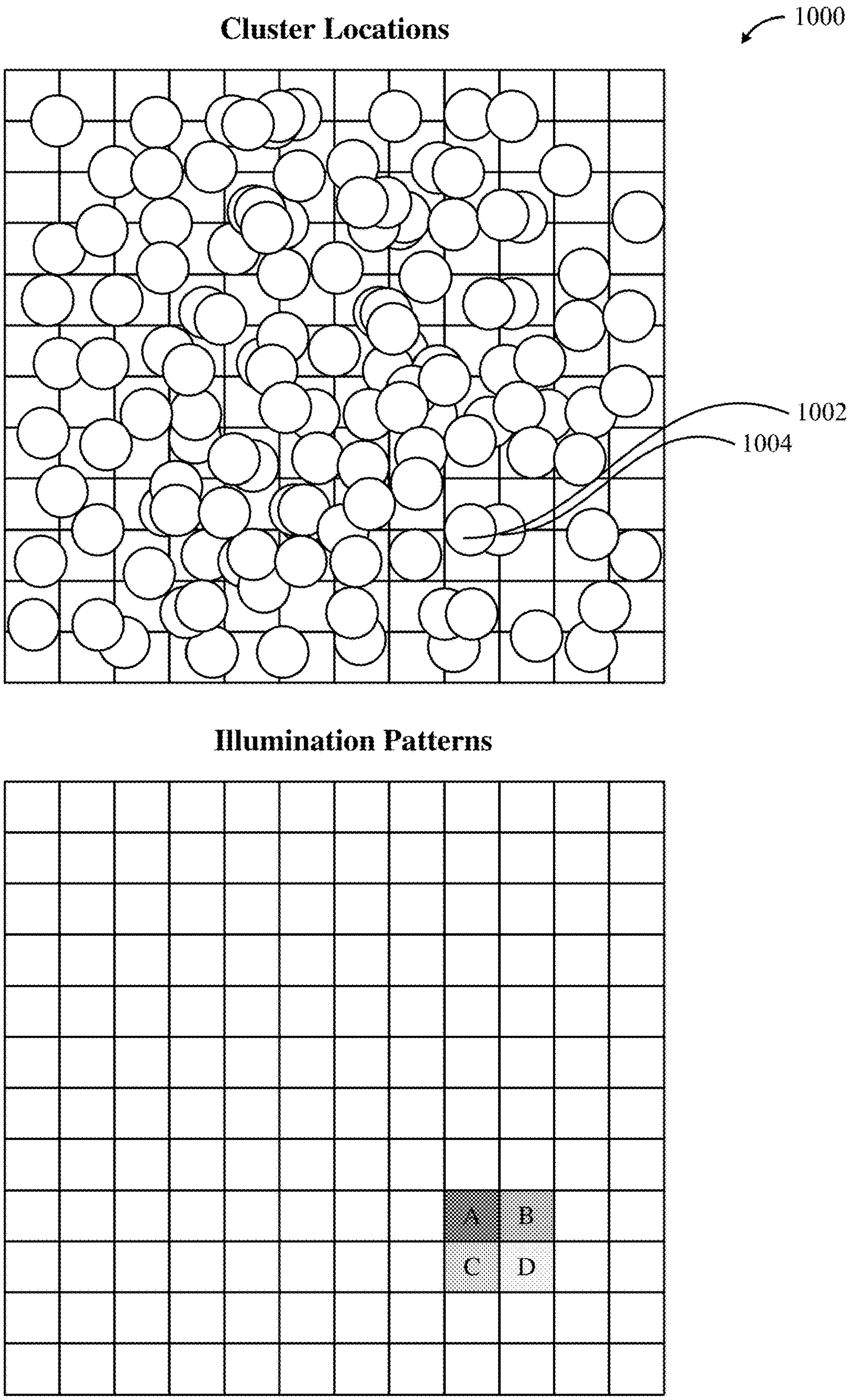

FIG. 10 illustrates a top plan view of a sample surface having pixel areas on which a plurality of clusters is unevenly distributed in accordance with one embodiment.

Figure 11A:
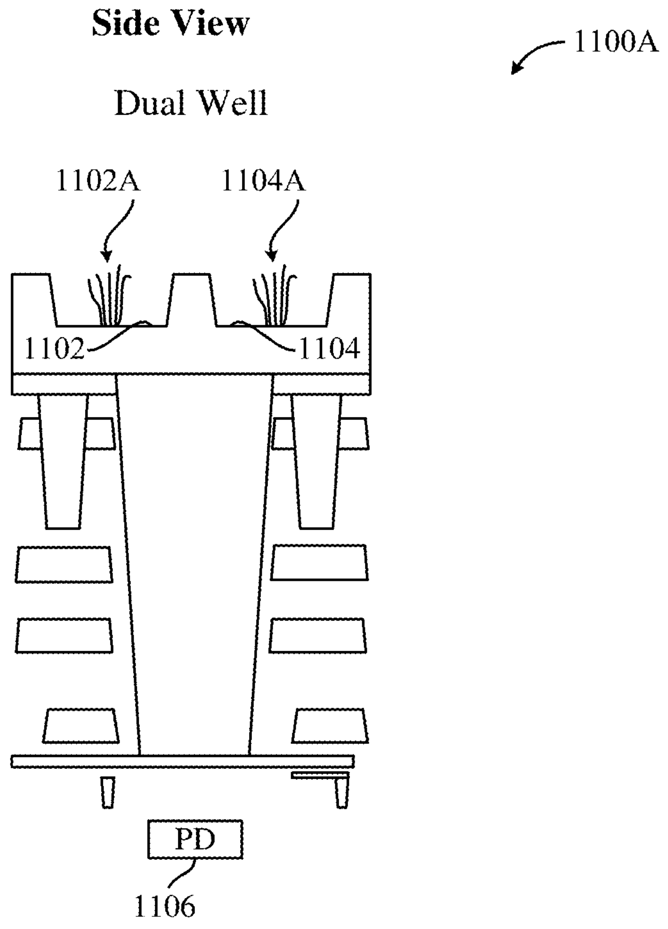

FIG. 11A illustrates a side view of a sample surface having two wells per pixel area including a dominant well and a subordinate well in accordance with one embodiment.

Figure 11B:
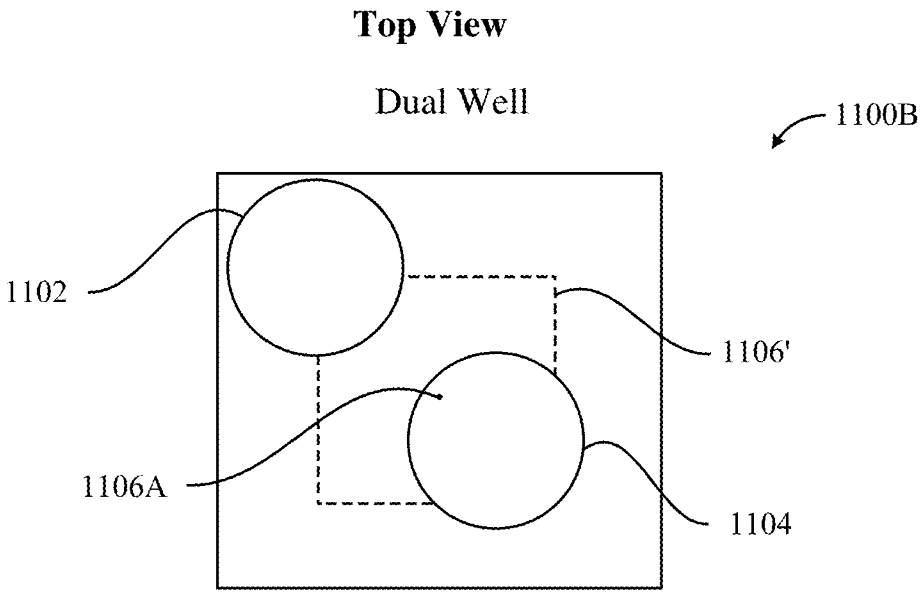

FIG. 11B depicts a top plan view of the sample surface of FIG. 11A.

Figure 12A:
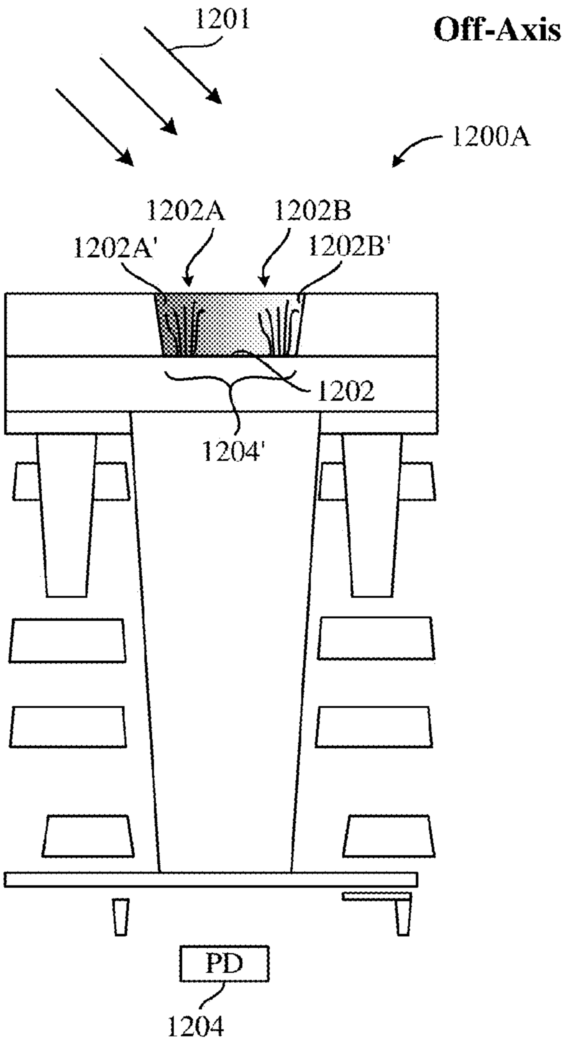
Figure 12B:
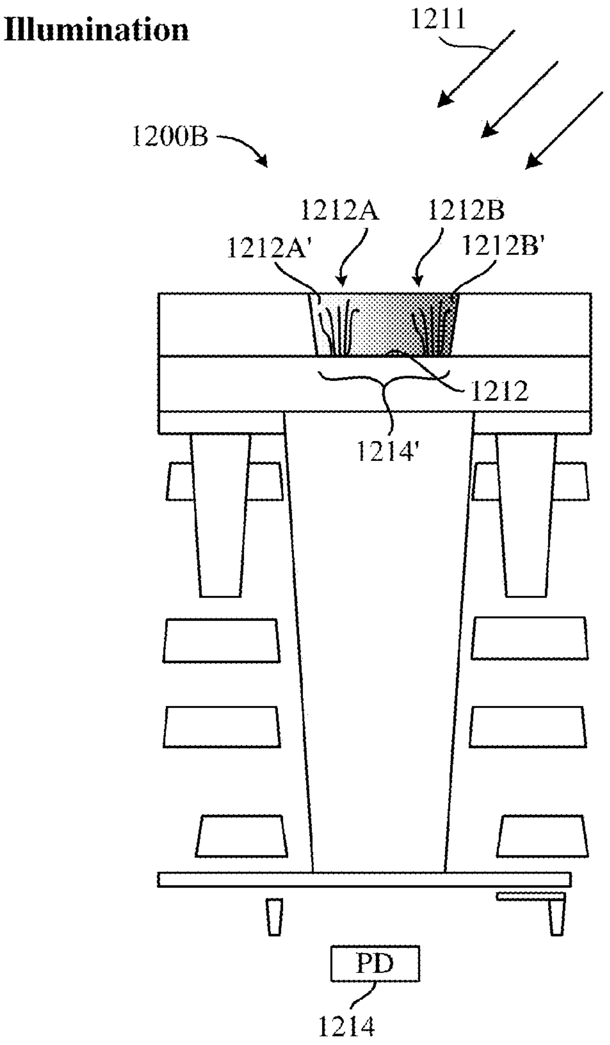

FIGS. 12A and 12B show off-axis illumination of a well overlying a pixel area of a sample surface.

Figure 12C:
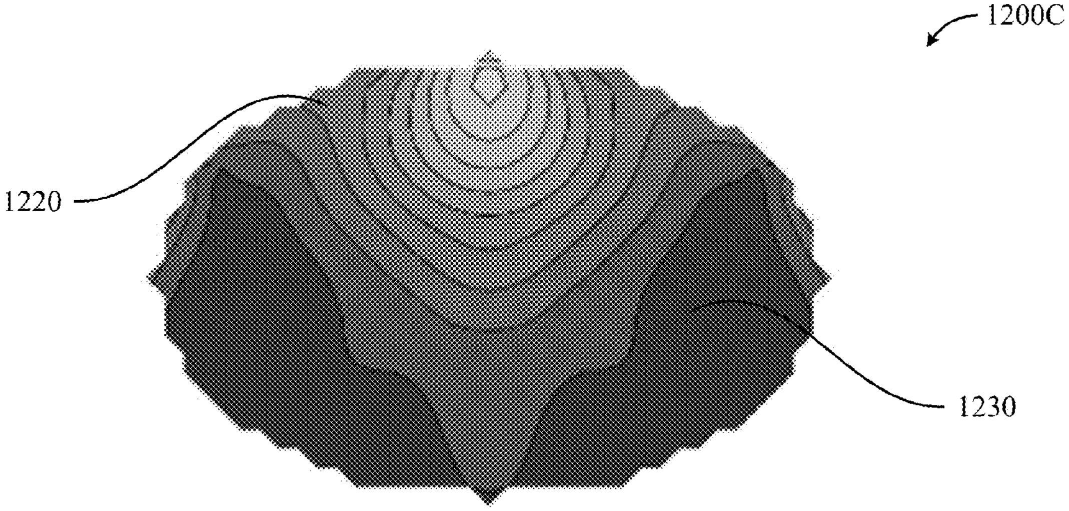

FIG. 12C illustrates asymmetrically illuminated well regions produced by the off-axis illumination of FIGS. 12A and 12B in accordance with one embodiment.

DETAILED DESCRIPTION

Embodiments described herein may be used in various biological or chemical processes and systems for academic or commercial analysis. More specifically, embodiments described herein may be used in various processes and systems where it is desired to detect an event, property, quality, or characteristic that is indicative of a desired reaction. For example, embodiments described herein include cartridges, biosensors, and their components as well as bioassay systems that operate with cartridges and biosensors. In particular embodiments, the cartridges and biosensors include a flow cell and one or more sensors, pixels, light detectors, or photodiodes that are coupled together in a substantially unitary structure.

The bioassay systems may be configured to perform a plurality of desired reactions that may be detected individually or collectively. The biosensors and bioassay systems may be configured to perform numerous cycles in which the plurality of desired reactions occurs in parallel. For example, the bioassay systems may be used to sequence a dense array of DNA features through iterative cycles of enzymatic manipulation and data acquisition. As such, the cartridges and biosensors may include one or more microfluidic channels that deliver reagents or other reaction components to a reaction site. In some embodiments, the reaction sites are unevenly distributed across a substantially planar surface. In other embodiments, the reaction sites are patterned across a substantially planar surface in a predetermined manner. Each of the reaction sites may be associated with one or more sensors, pixels, light detectors, or photodiodes that detect light from the associated reaction site. Yet in other embodiments, the reaction sites are located in reaction chambers (or wells) that compartmentalize the desired reactions therein.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be standalone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" or "including" an element or a plurality of elements having a particular property may include additional elements whether or not they have that property.

As used herein, a "desired reaction" includes a change in at least one of a chemical, electrical, physical, or optical property (or quality) of an analyte-of-interest. In particular embodiments, the desired reaction is a positive binding event (e.g., incorporation of a fluorescently labeled biomolecule with the analyte-of-interest). More generally, the desired reaction may be a chemical transformation, chemical change, or chemical interaction. The desired reaction may also be a change in electrical properties. For example, the desired reaction may be a change in ion concentration within a solution. Exemplary reactions include, but are not limited to, chemical reactions such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding. The desired reaction can also be an addition or elimination of a proton, for example, detectable as a change in pH of a surrounding solution or environment. An additional desired reaction can be detecting the flow of ions across a membrane (e.g., natural or synthetic bilayer membrane), for example as ions flow through a membrane the current is disrupted and the disruption can be detected.

In particular embodiments, the desired reaction includes the incorporation of a fluorescently-labeled molecule to an analyte. The analyte may be an oligonucleotide and the fluorescently-labeled molecule may be a nucleotide. The desired reaction may be detected when an excitation light is directed toward the oligonucleotide having the labeled nucleotide, and the fluorophore emits a detectable fluorescent signal. In alternative embodiments, the detected fluorescence is a result of chemiluminescence or bioluminescence. A desired reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a “reaction component” or “reactant” includes any substance that may be used to obtain a desired reaction. For example, reaction components include reagents, enzymes, samples, other biomolecules, and buffer solutions. The reaction components are typically delivered to a reaction site in a solution and/or immobilized at a reaction site. The reaction components may interact directly or indirectly with another substance, such as the analyte-of-interest.

As used herein, the term “reaction site” is a localized region where a desired reaction may occur. A reaction site may include support surfaces of a substrate where a substance may be immobilized thereon. For example, a reaction site may include a substantially planar surface in a channel of a flow cell that has a colony of nucleic acids thereon. Typically, but not always, the nucleic acids in the colony have the same sequence, being for example, clonal copies of a single stranded or double stranded template. However, in some embodiments a reaction site may contain only a single nucleic acid molecule, for example, in a single stranded or double stranded form. Furthermore, a plurality of reaction sites may be unevenly distributed along the support surface or arranged in a predetermined manner (e.g., side-by-side in a matrix, such as in microarrays). A reaction site can also include a reaction chamber (or well) that at least partially defines a spatial region or volume configured to compartmentalize the desired reaction.

This application uses the terms “reaction chamber” and “well” interchangeably. As used herein, the term “reaction chamber” or “well” includes a spatial region that is in fluid communication with a flow channel. The reaction chamber may be at least partially separated from the surrounding environment or other spatial regions. For example, a plurality of reaction chambers may be separated from each other by shared walls. As a more specific example, the reaction chamber may include a cavity defined by interior surfaces of a well and have an opening or aperture so that the cavity may be in fluid communication with a flow channel. Biosensors including such reaction chambers are described in greater detail in international application no. PCT/US2011/057111, filed on Oct. 20, 2011, which is incorporated herein by reference in its entirety.

In some embodiments, the reaction chambers are sized and shaped relative to solids (including semi-solids) so that the solids may be inserted, fully or partially, therein. For example, the reaction chamber may be sized and shaped to accommodate only one capture bead. The capture bead may have clonally amplified DNA or other substances thereon. Alternatively, the reaction chamber may be sized and shaped to receive an approximate number of beads or solid substrates. As another example, the reaction chambers may also be filled with a porous gel or substance that is configured to control diffusion or filter fluids that may flow into the reaction chamber.

In some embodiments, sensors (e.g., light detectors, photodiodes) are associated with corresponding pixel areas of a sample surface of a biosensor. As such, a pixel area is a geometrical construct that represents an area on the biosensor’s sample surface for one sensor (or pixel). A sensor that is associated with a pixel area detects light emissions gathered from the associated pixel area when a desired reaction has occurred at a reaction site or a reaction chamber overlying the associated pixel area. In a flat surface embodiment, the pixel areas can overlap. In some cases, a plurality of sensors may be associated with a single reaction site or a single reaction chamber. In other cases, a single sensor may be associated with a group of reaction sites or a group of reaction chambers.

As used herein, a “biosensor” includes a structure having a plurality of reaction sites and/or reaction chambers (or wells). A biosensor may include a solid-state imaging device (e.g., CCD or CMOS imager) and, optionally, a flow cell mounted thereto. The flow cell may include at least one flow channel that is in fluid communication with the reaction sites and/or the reaction chambers. As one specific example, the biosensor is configured to fluidically and electrically couple to a bioassay system. The bioassay system may deliver reactants to the reaction sites and/or the reaction chambers according to a predetermined protocol (e.g., sequencing-by-synthesis) and perform a plurality of imaging events. For example, the bioassay system may direct solutions to flow along the reaction sites and/or the reaction chambers. At least one of the solutions may include four types of nucleotides having the same or different fluorescent labels. The nucleotides may bind to corresponding oligonucleotides located at the reaction sites and/or the reaction chambers. The bioassay system may then illuminate the reaction sites and/or the reaction chambers using an excitation light source (e.g., solid-state light sources, such as light-emitting diodes or LEDs). The excitation light may have a predetermined wavelength or wavelengths, including a range of wavelengths. The excited fluorescent labels provide emission signals that may be captured by the sensors.

In alternative embodiments, the biosensor may include electrodes or other types of sensors configured to detect other identifiable properties. For example, the sensors may be configured to detect a change in ion concentration. In another example, the sensors may be configured to detect the ion current flow across a membrane.

As used herein, a “cartridge” includes a structure that is configured to hold a biosensor. In some embodiments, the cartridge may include additional features, such as the light source (e.g., LEDs) that are configured to provide excitation light to the reaction sites and/or the reaction chambers of the biosensor. The cartridge may also include a fluidic storage system (e.g., storage for reagents, sample, and buffer) and a fluidic control system (e.g., pumps, valves, and the like) for fluidically transporting reaction components, sample, and the like to the reaction sites and/or the reaction chambers. For example, after the biosensor is prepared or manufactured, the biosensor may be coupled to a housing or container of the cartridge. In some embodiments, the biosensors and the cartridges may be self-contained, disposable units. However, other embodiments may include an assembly with removable parts that allow a user to access an interior of the biosensor or cartridge for maintenance or replacement of components or samples. The biosensor and the cartridge may be removably coupled or engaged to larger bioassay systems, such as a sequencing system, that conducts controlled reactions therein.

As used herein, when the terms "removably" and "coupled" (or "engaged") are used together to describe a relationship between the biosensor (or cartridge) and a system receptacle or interface of a bioassay system, the term is intended to mean that a connection between the biosensor (or cartridge) and the system receptacle is readily separable without destroying or damaging the system receptacle and/or the biosensor (or cartridge). Components are readily separable when the components may be separated from each other without undue effort or a significant amount of time spent in separating the components. For example, the biosensor (or cartridge) may be removably coupled or engaged to the system receptacle in an electrical manner such that the mating contacts of the bioassay system are not destroyed or damaged. The biosensor (or cartridge) may also be removably coupled or engaged to the system receptacle in a mechanical manner such that the features that hold the biosensor (or cartridge) are not destroyed or damaged. The biosensor (or cartridge) may also be removably coupled or engaged to the system receptacle in a fluidic manner such that the ports of the system receptacle are not destroyed or damaged. The system receptacle or a component is not considered to be destroyed or damaged if, for example, only a simple adjustment to the component (e.g., realignment) or a simple replacement (e.g., replacing a nozzle) is required.

As used herein, a "cluster" is a colony of similar or identical molecules or nucleotide sequences or DNA strands. For example, a cluster can be an amplified oligonucleotide or any other group of a polynucleotide or polypeptide with a same or similar sequence. In other embodiments, a cluster can be any element or group of elements that occupy a physical area on a sample surface. In embodiments, clusters are immobilized to a reaction site and/or a reaction chamber during a base calling cycle.

As used herein, the term "immobilized," when used with respect to a biomolecule or biological or chemical substance, includes substantially attaching the biomolecule or biological or chemical substance at a molecular level to a surface. For example, a biomolecule or biological or chemical substance may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to a surface of a substrate material may be based upon the properties of the substrate surface, the liquid medium carrying the biomolecule or biological or chemical substance, and the properties of the biomolecules or biological or chemical substances themselves. In some cases, a substrate surface may be functionalized (e.g., chemically or physically modified) to facilitate immobilizing the biomolecules (or biological or chemical substances) to the substrate surface. The substrate surface may be first modified to have functional groups bound to the surface. The functional groups may then bind to biomolecules or biological or chemical substances to immobilize them thereon. A substance can be immobilized to a surface via a gel, for example, as described in US Patent Publ. No. US 2011/0059865 A1, which is incorporated herein by reference.

In some embodiments, nucleic acids can be attached to a surface and amplified using bridge amplification. Useful bridge amplification methods are described, for example, in U.S. Pat. No. 5,641,658; WO 2007/010251, U.S. Pat. No. 6,090,592; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein in its entirety. Another useful method for amplifying nucleic acids on a surface is rolling circle amplification (RCA), for example, using methods set forth in further detail below. In some embodiments, the nucleic acids can be attached to a surface and amplified using one or more primer pairs. For example, one of the primers can be in solution and the other primer can be immobilized on the surface (e.g., 5'-attached). By way of example, a nucleic acid molecule can hybridize to one of the primers on the surface followed by extension of the immobilized primer to produce a first copy of the nucleic acid. The primer in solution then hybridizes to the first copy of the nucleic acid which can be extended using the first copy of the nucleic acid as a template. Optionally, after the first copy of the nucleic acid is produced, the original nucleic acid molecule can hybridize to a second immobilized primer on the surface and can be extended at the same time or after the primer in solution is extended. In any embodiment, repeated rounds of extension (e.g., amplification) using the immobilized primer and primer in solution provide multiple copies of the nucleic acid.

In particular embodiments, the assay protocols executed by the systems and methods described herein include the use of natural nucleotides and also enzymes that are configured to interact with the natural nucleotides. Natural nucleotides include, for example, ribonucleotides (RNA) or deoxyribonucleotides (DNA). Natural nucleotides can be in the mono-, di-, or tri-phosphate form and can have a base selected from adenine (A), thymine (T), uracil (U), guanine (G) or cytosine (C). It will be understood however that non-natural nucleotides, modified nucleotides or analogs of the aforementioned nucleotides can be used. Some examples of useful non-natural nucleotides are set forth below in regard to reversible terminator-based sequencing by synthesis methods.

In embodiments that include reaction chambers, items or solid substances (including semi-solid substances) may be disposed within the reaction chambers. When disposed, the item or solid may be physically held or immobilized within the reaction chamber through an interference fit, adhesion, or entrapment. Exemplary items or solids that may be disposed within the reaction chambers include polymer beads, pellets, agarose gel, powders, quantum dots, or other solids that may be compressed and/or held within the reaction chamber. In particular embodiments, a nucleic acid superstructure, such as a DNA ball, can be disposed in or at a reaction chamber, for example, by attachment to an interior surface of the reaction chamber or by residence in a liquid within the reaction chamber. A DNA ball or other nucleic acid superstructure can be preformed and then disposed in or at the reaction chamber. Alternatively, a DNA ball can be synthesized in situ at the reaction chamber. A DNA ball can be synthesized by rolling circle amplification to produce a concatamer of a particular nucleic acid sequence and the concatamer can be treated with conditions that form a relatively compact ball. DNA balls and methods for their synthesis are described, for example in, U.S. Patent Publication Nos. 2008/0242560 A1 or 2008/0234136 A1, each of which is incorporated herein in its entirety. A substance that is held or disposed in a reaction chamber can be in a solid, liquid, or gaseous state.

As used herein, "base calling" identifies a nucleotide base in a nucleic acid sequence. Base calling refers to the process of determining a base call (A, C, G, T) for every cluster at a specific cycle. As an example, base calling can be performed utilizing four-channel, two-channel or one-channel methods and systems described in the incorporated materials of U.S. Patent Application Publication No. 2013/0079232. In particular embodiments, a base calling cycle is referred to as a "sampling event." In one dye and two-channel sequencing protocol, a sampling event comprises two illumination stages in time sequence, such that a pixel signal is generated at each stage. The first illumination stage induces illumination from a given cluster indicating nucleotide bases A and T in a AT pixel signal, and the second illumination stage induces illumination from a given cluster indicating nucleotide bases C and T in a CT pixel signal.

Base Calling System

FIG. 1 is a block diagram of a base calling system 100 in accordance with one embodiment. The base calling system 100 may operate to obtain any information or data that relates to at least one of a biological or chemical substance. In some embodiments, the base calling system 100 is a workstation that may be similar to a bench-top device or desktop computer. For example, a majority (or all) of the systems and components for conducting the desired reactions can be within a common housing 116.

In particular embodiments, the base calling system 100 is a nucleic acid sequencing system (or sequencer) configured for various applications, including but not limited to de novo sequencing, resequencing of whole genomes or target genomic regions, and metagenomics. The sequencer may also be used for DNA or RNA analysis. In some embodiments, the base calling system 100 may also be configured to generate reaction sites in a biosensor. For example, the base calling system 100 may be configured to receive a sample and generate surface attached clusters of clonally amplified nucleic acids derived from the sample. Each cluster may constitute or be part of a reaction site in the biosensor.

The exemplary base calling system 100 may include a system receptacle or interface 112 that is configured to interact with a biosensor 102 to perform desired reactions within the biosensor 102. In the following description with respect to FIG. 1, the biosensor 102 is loaded into the system receptacle 112. However, it is understood that a cartridge that includes the biosensor 102 may be inserted into the system receptacle 112 and in some states the cartridge can be removed temporarily or permanently. As described above, the cartridge may include, among other things, fluidic control and fluidic storage components.

In particular embodiments, the base calling system 100 is configured to perform a large number of parallel reactions within the biosensor 102. The biosensor 102 includes one or more reaction sites where desired reactions can occur. The reaction sites may be, for example, immobilized to a solid surface of the biosensor or immobilized to beads (or other movable substrates) that are located within corresponding reaction chambers of the biosensor. The reaction sites can include, for example, clusters of clonally amplified nucleic acids. The biosensor 102 may include a solid-state imaging device (e.g., CCD or CMOS imager) and a flow cell mounted thereto. The flow cell may include one or more flow channels that receive a solution from the base calling system 100 and direct the solution toward the reaction sites. Optionally, the biosensor 102 can be configured to engage a thermal element for transferring thermal energy into or out of the flow channel.

The base calling system 100 may include various components, assemblies, and systems (or sub-systems) that interact with each other to perform a predetermined method or assay protocol for biological or chemical analysis. For example, the base calling system 100 includes a system controller 104 that may communicate with the various components, assemblies, and sub-systems of the base calling system 100 and also the biosensor 102. For example, in addition to the system receptacle 112, the base calling system 100 may also include a fluidic control system 106 to control the flow of fluid throughout a fluid network of the base calling system 100 and the biosensor 102; a fluid storage system 108 that is configured to hold all fluids (e.g., gas or liquids) that may be used by the bioassay system; a temperature control system 110 that may regulate the temperature of the fluid in the fluid network, the fluid storage system 108, and/or the biosensor 102; and an illumination system 109 that is configured to illuminate the biosensor 102. As described above, if a cartridge having the biosensor 102 is loaded into the system receptacle 112, the cartridge may also include fluidic control and fluidic storage components.

Also shown, the base calling system 100 may include a user interface 114 that interacts with the user. For example, the user interface 114 may include a display 113 to display or request information from a user and a user input device 115 to receive user inputs. In some embodiments, the display 113 and the user input device 115 are the same device. For example, the user interface 114 may include a touch-sensitive display configured to detect the presence of an individual's touch and also identify a location of the touch on the display. However, other user input devices 115 may be used, such as a mouse, touchpad, keyboard, keypad, handheld scanner, voice-recognition system, motion-recognition system, and the like. As will be discussed in greater detail below, the base calling system 100 may communicate with various components, including the biosensor 102 (e.g., in the form of a cartridge), to perform the desired reactions. The base calling system 100 may also be configured to analyze data obtained from the biosensor to provide a user with desired information.

The system controller 104 may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. The above examples are exemplary only, and are thus not intended to limit in any way the definition and/or meaning of the term system controller. In the exemplary embodiment, the system controller 104 executes a set of instructions that are stored in one or more storage elements, memories, or modules in order to at least one of obtain and analyze detection data. Detection data can include a plurality of sequences of pixel signals, such that a sequence of pixel signals from each of the millions of sensors (or pixels) can be detected over many base calling cycles. Storage elements may be in the form of information sources or physical memory elements within the base calling system 100.

The set of instructions may include various commands that instruct the base calling system 100 or biosensor 102 to perform specific operations such as the methods and processes of the various embodiments described herein. The set of instructions may be in the form of a software program, which may form part of a tangible, non-transitory computer readable medium or media. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the base calling system 100, processed in response to user inputs, or processed in response to a request made by another processing machine (e.g., a remote request through a communication link). In the illustrated embodiment, the system controller 104 includes the signal processor 138. In other embodiments, system controller 104 does not include the signal processor 138 and instead has access to the signal processor 138 (e.g., the signal processor 138 may be separately hosted on cloud).

The system controller 104 may be connected to the biosensor 102 and the other components of the base calling system 100 via communication links. The system controller 104 may also be communicatively connected to off-site systems or servers. The communication links may be hardwired, corded, or wireless. The system controller 104 may receive user inputs or commands, from the user interface 114 and the user input device 115.

The fluidic control system 106 includes a fluid network and is configured to direct and regulate the flow of one or more fluids through the fluid network. The fluid network may be in fluid communication with the biosensor 102 and the fluid storage system 108. For example, select fluids may be drawn from the fluid storage system 108 and directed to the biosensor 102 in a controlled manner, or the fluids may be drawn from the biosensor 102 and directed toward, for example, a waste reservoir in the fluid storage system 108. Although not shown, the fluidic control system 106 may include flow sensors that detect a flow rate or pressure of the fluids within the fluid network. The sensors may communicate with the system controller 104.

The temperature control system 110 is configured to regulate the temperature of fluids at different regions of the fluid network, the fluid storage system 108, and/or the biosensor 102. For example, the temperature control system 110 may include a thermocycler that interfaces with the biosensor 102 and controls the temperature of the fluid that flows along the reaction sites in the biosensor 102. The temperature control system 110 may also regulate the temperature of solid elements or components of the base calling system 100 or the biosensor 102. Although not shown, the temperature control system 110 may include sensors to detect the temperature of the fluid or other components. The sensors may communicate with the system controller 104.

The fluid storage system 108 is in fluid communication with the biosensor 102 and may store various reaction components or reactants that are used to conduct the desired reactions therein. The fluid storage system 108 may also store fluids for washing or cleaning the fluid network and biosensor 102 and for diluting the reactants. For example, the fluid storage system 108 may include various reservoirs to store samples, reagents, enzymes, other biomolecules, buffer solutions, aqueous, and non-polar solutions, and the like. Furthermore, the fluid storage system 108 may also include waste reservoirs for receiving waste products from the biosensor 102. In embodiments that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 109 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In embodiments that use an illumination system, the illumination system 109 may be configured to direct an excitation light to reaction sites. As one example, fluorophores may be excited by green wavelengths of light, as such the wavelength of the excitation light may be approximately 532 nm. In one embodiment, the illumination system 109 is configured to produce illumination that is parallel to a surface normal of a surface of the biosensor 102. In another embodiment, the illumination system 109 is configured to produce illumination that is off-angle relative to the surface normal of the surface of the biosensor 102. In yet another embodiment, the illumination system 109 is configured to produce illumination that has plural angles, including some parallel illumination and some off-angle illumination.

The system receptacle or interface 112 is configured to engage the biosensor 102 in at least one of a mechanical, electrical, and fluidic manner. The system receptacle 112 may hold the biosensor 102 in a desired orientation to facilitate the flow of fluid through the biosensor 102. The system receptacle 112 may also include electrical contacts that are configured to engage the biosensor 102 so that the base calling system 100 may communicate with the biosensor 102 and/or provide power to the biosensor 102. Furthermore, the system receptacle 112 may include fluidic ports (e.g., nozzles) that are configured to engage the biosensor 102. In some embodiments, the biosensor 102 is removably coupled to the system receptacle 112 in a mechanical manner, in an electrical manner, and also in a fluidic manner.

In addition, the base calling system 100 may communicate remotely with other systems or networks or with other bioassay systems 100. Detection data obtained by the bioassay system(s) 100 may be stored in a remote database.

FIG. 2 is a block diagram of a system controller 104 that can be used in the system of FIG. 1. In one embodiment, the system controller 104 includes one or more processors or modules that can communicate with one another. Each of the processors or modules may include an algorithm (e.g., instructions stored on a tangible and/or non-transitory computer readable storage medium) or sub-algorithms to perform particular processes. The system controller 104 is illustrated conceptually as a collection of modules, but may be implemented utilizing any combination of dedicated hardware boards, DSPs, processors, etc. Alternatively, the system controller 104 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication port 120 may transmit information (e.g. commands) to or receive information (e.g., data) from the biosensor 102 (FIG. 1) and/or the sub-systems 106, 108, 110 (FIG. 1). In embodiments, the communication port 120 may output a plurality of sequences of pixel signals. A communication link 122 may receive user input from the user interface 114 (FIG. 1) and transmit data or information to the user interface 114. Data from the biosensor 102 or sub-systems 106, 108, 110 may be processed by the system controller 104 in real-time during a bioassay session. Additionally or alternatively, data may be stored temporarily in a system memory during a bioassay session and processed in slower than real-time or off-line operation.

As shown in FIG. 2, the system controller 104 may include a plurality of modules 131-139 that communicate with a main control module 130. The main control module 130 may communicate with the user interface 114 (FIG. 1). Although the modules 131-139 are shown as communicating directly with the main control module 130, the modules 131-139 may also communicate directly with each other, the user interface 114, and the biosensor 102. Also, the modules 131-139 may communicate with the main control module 130 through the other modules.

The plurality of modules 131-139 include system modules 131-133, 139 that communicate with the sub-systems 106, 108, 110, and 111, respectively. The fluidic control module 131 may communicate with the fluidic control system 106 to control the valves and flow sensors of the fluid network for controlling the flow of one or more fluids through the fluid network. The fluid storage module 132 may notify the user when fluids are low or when the waste reservoir is at or near capacity. The fluid storage module 132 may also communicate with the temperature control module 133 so that the fluids may be stored at a desired temperature. The illumination module 139 may communicate with the illumination system 109 to illuminate the reaction sites at designated times during a protocol, such as after the desired reactions (e.g., binding events) have occurred. In some embodiments, the illumination module 139 may communicate with the illumination system 109 to illuminate the reaction sites at designated angles.

The plurality of modules 131-139 may also include a device module 134 that communicates with the biosensor 102 and an identification module 135 that determines identification information relating to the biosensor 102. The device module 134 may, for example, communicate with the system receptacle 112 to confirm that the biosensor has established an electrical and fluidic connection with the base calling system 100. The identification module 135 may receive signals that identify the biosensor 102. The identification module 135 may use the identity of the biosensor 102 to provide other information to the user. For example, the identification module 135 may determine and then display a lot number, a date of manufacture, or a protocol that is recommended to be run with the biosensor 102.

The plurality of modules 131-139 may also include a signal processing module or signal processor 138 that receives and analyzes the signal data (e.g., image data) from the biosensor 102. Signal processor 138 includes memory 140 (e.g., RAM or Flash) to store detection data. Detection data can include a plurality of sequences of pixel signals, such that a sequence of pixel signals from each of the millions of sensors (or pixels) can be detected over many base calling cycles. The signal data may be stored for subsequent analysis or may be transmitted to the user interface 114 to display desired information to the user. In some embodiments, the signal data may be processed by the solid-state imager (e.g., CMOS image sensor) before the signal processor 138 receives the signal data.

Protocol modules 136 and 137 communicate with the main control module 130 to control the operation of the sub-systems 106, 108, and 110 when conducting predetermined assay protocols. The protocol modules 136 and 137 may include sets of instructions for instructing the base calling system 100 to perform specific operations pursuant to predetermined protocols. As shown, the protocol module may be a sequencing-by-synthesis (SBS) module 136 that is configured to issue various commands for performing sequencing-by-synthesis processes. In SBS, extension of a nucleic acid primer along a nucleic acid template is monitored to determine the sequence of nucleotides in the template. The underlying chemical process can be polymerization (e.g. as catalyzed by a polymerase enzyme) or ligation (e.g. catalyzed by a ligase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated can be detected through an imaging event. During an imaging event, the illumination system 109 may provide an excitation light to the reaction sites. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination a command can be given to deliver a deblocking reagent to the flow cell (before or after detection occurs). One or more commands can be given to effect wash(es) between the various delivery steps. The cycle can then be repeated n times to extend the primer by n nucleotides, thereby detecting a sequence of length n. Exemplary sequencing techniques are described, for example, in Bentley et al., Nature 456:53-59 (2008), WO 2004/018497; U.S. Pat. No. 7,057,026; WO 91/06678; WO 2007/123744; U.S. Pat. Nos. 7,329,492; 7,211,414; 7,315,019; 7,405,281, and US 2008/0108082, each of which is incorporated herein by reference.

For the nucleotide delivery step of an SBS cycle, either a single type of nucleotide can be delivered at a time, or multiple different nucleotide types (e.g. A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one embodiment, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In some embodiments, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in U.S. Patent Application Ser. Nos. 61/538,294 and 61/619,878, which are incorporated herein by reference in their entireties. U.S. application Ser. No. 13/624,200, which was filed on Sep. 21, 2012, is relevant in this context and also incorporated by reference in its entirety.

The plurality of protocol modules may also include a sample-preparation (or generation) module 137 that is configured to issue commands to the fluidic control system 106 and the temperature control system 110 for amplifying a product within the biosensor 102. For example, the biosensor 102 may be engaged to the base calling system 100. The amplification module 137 may issue instructions to the fluidic control system 106 to deliver necessary amplification components to reaction chambers within the biosensor 102. In other embodiments, the reaction sites may already contain some components for amplification, such as the template DNA and/or primers. After delivering the amplification components to the reaction chambers, the amplification module 137 may instruct the temperature control system 110 to cycle through different temperature stages according to known amplification protocols. In some embodiments, the amplification and/or nucleotide incorporation is performed isothermally.

The SBS module 136 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method can be used as set forth above or as follows.

Each base calling or sequencing cycle can extend a sstDNA by a single base which can be accomplished for example by using a modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar base calling or sequencing cycle may follow. In such a sequencing protocol, the SBS module 136 may instruct the fluidic control system 106 to direct a flow of reagent and enzyme solutions through the biosensor 102. Exemplary reversible terminator-based SBS methods which can be utilized with the apparatus and methods set forth herein are described in US Patent Application Publication No. 2007/0166705 A1, US Patent Application Publication No. 2006/0188901 A1, U.S. Pat. No. 7,057,026, US Patent Application Publication No. 2006/0240439 A1, US Patent Application Publication No. 2006/0281109 A1, PCT Publication No. WO 2005/065814, US Patent Application Publication No. 2005/0100900 A1, PCT Publication No. WO 2006/064199 and PCT Publication No. WO 2007/010251, each of which is incorporated herein by reference in its entirety. Exemplary reagents for reversible terminator-based SBS are described in U.S. Pat. Nos. 7,541,444; 7,057,026; 7,414,116; 7,427,673; 7,566,537; 7,592,435 and WO 2007/135368, each of which is incorporated herein by reference in its entirety.

In some embodiments, the amplification and SBS modules may operate in a single assay protocol where, for example, template nucleic acid is amplified and subsequently sequenced within the same cartridge.

The base calling system 100 may also allow the user to reconfigure an assay protocol. For example, the base calling system 100 may offer options to the user through the user interface 114 for modifying the determined protocol. For example, if it is determined that the biosensor 102 is to be used for amplification, the base calling system 100 may request a temperature for the annealing cycle. Furthermore, the base calling system 100 may issue warnings to a user if a user has provided user inputs that are generally not acceptable for the selected assay protocol.

In embodiments, the biosensor 102 includes millions of sensors (or pixels), each of which generates a plurality of sequences of pixel signals over successive base calling cycles. Signal processor 130 detects the plurality of sequences of pixel signals and attributes them to corresponding sensors (or pixels) in accordance to the row-wise and/or column-wise location of the sensors on an array of sensors.

Biosensor

FIG. 3 illustrates a cross-section of a biosensor 300 that can be used in various embodiments. Biosensor 300 has pixel areas 306', 308', 310', 312', and 314' that can each hold more than one cluster during a base calling cycle (e.g., 2 clusters per pixel area). Biosensor 300 may have similar features as the biosensor 102 (FIG. 1) described above and may be used in, for example, the cartridge. As shown, the biosensor 300 may include a flow cell 302 that is mounted onto a sampling device 304. In the illustrated embodiment, the flow cell 302 is affixed directly to the sampling device 304. However, in alternative embodiments, the flow cell 302 may be removably coupled to the sampling device 304. The sampling device 304 has a sample surface 334 that may be functionalized (e.g., chemically or physically modified in a suitable manner for conducting the desired reactions). For example, the sample surface 334 may be functionalized and may include a plurality of pixel areas 306', 308', 310', 312', and 314' that can each hold more than one cluster during a base calling cycle (e.g., each having a corresponding cluster pair 306AB, 308AB, 310AB, 312AB, and 314AB immobilized thereto). Each pixel area is associated with a corresponding sensor (or pixel or photodiode) 306, 308, 310, 312, and 314, such that light received by the pixel area is captured by the corresponding sensor. A pixel area 306' can be also associated with a corresponding reaction site 306" on the sample surface 334 that holds a cluster pair, such that light emitted from the reaction site 306" is received by the pixel area 306' and captured by the corresponding sensor 306. As a result of this sensing structure, in the case in which two or more clusters are present in a pixel area of a particular sensor during a base calling cycle (e.g., each having a corresponding cluster pair), the pixel signal in that base calling cycle carries information based on all of the two or more clusters. As a result, signal processing as described herein is used to distinguish each cluster, where there are more clusters than pixel signals in a given sampling event of a particular base calling cycle.

In the illustrated embodiment, the flow cell 302 includes sidewalls 338, 340 and a flow cover 336 that is supported by the sidewalls 338, 340. The sidewalls 338, 340 are coupled to the sample surface 334 and extend between the flow cover 336 and the sidewalls 338, 340. In some embodiments, the sidewalls 338, 340 are formed from a curable adhesive layer that bonds the flow cover 336 to the sampling device 304.

The sidewalls 338, 340 are sized and shaped so that a flow channel 344 exists between the flow cover 336 and the sampling device 304. As shown, the flow channel 344 may include a height $H_1$ that is determined by the sidewalls 338, 340. The height $H_1$ may be between about 50-400 μm (micrometer) or, more particularly, about 80-200 μm. In the illustrated embodiment, the height $H_1$ is about 100 μm. The flow cover 336 may include a material that is transparent to excitation light 301 propagating from an exterior of the biosensor 300 into the flow channel 344. As shown in FIG. 3, the excitation light 301 approaches the flow cover 336 at a non-orthogonal angle. However, this is only for illustrative purposes as the excitation light 301 may approach the flow cover 336 from different angles.

Also shown, the flow cover 336 may include inlet and outlet ports 342, 346 that are configured to fluidically engage other ports (not shown). For example, the other ports may be from the cartridge or the workstation. The flow channel 344 is sized and shaped to direct a fluid along the sample surface 334. The height $H_1$ and other dimensions of the flow channel 344 may be configured to maintain a substantially even flow of a fluid along the sample surface 334. The dimensions of the flow channel 344 may also be configured to control bubble formation.

As shown in exemplary FIG. 3, the sidewalls 338, 340 and the flow cover 336 are separate components that are coupled to each other. In alternative embodiments, the sidewalls 338, 340 and the flow cover 336 may be integrally formed such that the sidewalls 338, 340 and the flow cover 336 are formed from a continuous piece of material. By way of example, the flow cover 336 (or the flow cell 302) may comprise a transparent material, such as glass or plastic. The flow cover 336 may constitute a substantially rectangular block having a planar exterior surface and a planar inner surface that defines the flow channel 344. The block may be mounted onto the sidewalls 338, 340. Alternatively, the flow cell 302 may be etched to define the flow cover 336 and the sidewalls 338, 340. For example, a recess may be etched into the transparent material. When the etched material is mounted to the sampling device 304, the recess may become the flow channel 344.

The sampling device 304 may be similar to, for example, an integrated circuit comprising a plurality of stacked substrate layers 320-326. The substrate layers 320-326 may include a base substrate 320, a solid-state imager 322 (e.g., CMOS image sensor), a filter or light-management layer 324, and a passivation layer 326. It should be noted that the above is only illustrative and that other embodiments may include fewer or additional layers. Moreover, each of the substrate layers 320-326 may include a plurality of sublayers. As will be described in greater detail below, the sampling device 304 may be manufactured using processes that are similar to those used in manufacturing integrated circuits, such as CMOS image sensors and CCDs. For example, the substrate layers 320-326 or portions thereof may be grown, deposited, etched, and the like to form the sampling device 304.

The passivation layer 326 is configured to shield the filter layer 324 from the fluidic environment of the flow channel 344. In some cases, the passivation layer 326 is also configured to provide a solid surface (i.e., the sample surface 334) that permits biomolecules or other analytes-of-interest to be immobilized thereon. For example, each of the reaction sites may include a cluster of biomolecules that are immobilized to the sample surface 334. Thus, the passivation layer 326 may be formed from a material that permits the reaction sites to be immobilized thereto. The passivation layer 326 may also comprise a material that is at least transparent to a desired fluorescent light. By way of example, the passivation layer 326 may include silicon nitride (Si3N4) and/or silica (SiO2). However, other suitable material(s) may be used. In the illustrated embodiment, the passivation layer 326 may be substantially planar. However, in alternative embodiments, the passivation layer 326 may include recesses, such as pits, wells, grooves, and the like. In the illustrated embodiment, the passivation layer 326 has a thickness that is about 150-200 nm and, more particularly, about 170 nm.

The filter layer 324 may include various features that affect the transmission of light. In some embodiments, the filter layer 324 can perform multiple functions. For instance, the filter layer 324 may be configured to (a) filter unwanted light signals, such as light signals from an excitation light source; (b) direct emission signals from the reaction sites toward corresponding sensors 306, 308, 310, 312, and 314 that are configured to detect the emission signals from the reaction sites; or (c) block or prevent detection of unwanted emission signals from adjacent reaction sites. As such, the filter layer 324 may also be referred to as a light-management layer. In the illustrated embodiment, the filter layer 324 has a thickness that is about 1-5 μm and, more particularly, about 3-4 μm. In alternative embodiments, the filter layer 324 may include an array of microlenses or other optical components. Each of the microlenses may be configured to direct emission signals from an associated reaction site to a sensor.

In some embodiments, the solid-state imager 322 and the base substrate 320 may be provided together as a previously constructed solid-state imaging device (e.g., CMOS chip). For example, the base substrate 320 may be a wafer of silicon and the solid-state imager 322 may be mounted thereon. The solid-state imager 322 includes a layer of semiconductor material (e.g., silicon) and the sensors 306, 308, 310, 312, and 314. In the illustrated embodiment, the sensors are photodiodes configured to detect light. In other embodiments, the sensors comprise light detectors. The solid-state imager 322 may be manufactured as a single chip through a CMOS-based fabrication processes.

The solid-state imager 322 may include a dense array of sensors 306, 308, 310, 312, and 314 that are configured to detect activity indicative of a desired reaction from within or along the flow channel 344. In some embodiments, each sensor has a pixel area (or detection area) that is about 1-3 square micrometer ($\mu m^2$). The array can include 500,000 sensors, 5 million sensors, 10 million sensors, or even 130 million sensors. The sensors 306, 308, 310, 312, and 314 can be configured to detect a predetermined wavelength of light that is indicative of the desired reactions.

In some embodiments, the sampling device 304 includes a microcircuit arrangement, such as the microcircuit arrangement described in U.S. Pat. No. 7,595,883, which is incorporated herein by reference in the entirety. More specifically, the sampling device 304 may comprise an integrated circuit having a planar array of the sensors 306, 308, 310, 312, and 314. The array of the sensors 306, 308, 310, 312, and 314 can be communicatively coupled to a row decoder and a column amplifier or decoder. The column amplifier can also be communicatively coupled to a column analog-to-digital converter (Column ADC/Mux). Other circuitry may be coupled to the above components, including a digital signal processor and memory. Circuitry formed within the sampling device 304 may be configured for at least one of signal amplification, digitization, storage, and processing. The circuitry may collect and analyze the detected fluorescent light and generate pixel signals (or detection signals) for communicating detection data to the signal processor 138. The circuitry may also perform additional analog and/or digital signal processing in the sampling device 304. Sampling device 304 may include conductive vias 330 that perform signal routing (e.g., transmit the pixel signals to the signal processor 138). The pixel signals may also be transmitted through electrical contacts 332 of the sampling device 304.

However, the sampling device 304 is not limited to the above constructions or uses as described above. In alternative embodiments, the sampling device 304 may take other forms. For example, the sampling device 304 may comprise a CCD device, such as a CCD camera, that is coupled to a flow cell or is moved to interface with a flow cell having reaction sites therein. In other embodiments, the sampling device 304 may be a CMOS-fabricated sensor, including chemically sensitive field effect transistors (chemFET), ion-sensitive field effect transistors (ISFET), and/or metal oxide semiconductor field effect transistors (MOSFET). Such embodiments may include an array of field effect transistors (FET's) that may be configured to detect a change in electrical properties within the reaction chambers. For example, the FET's may detect at least one of a presence and concentration change of various analytes. By way of example, the array of FET's may monitor changes in hydrogen ion concentration. Such sampling devices are described in greater detail is U.S. Patent Application Publication No. 2009/0127589, which is incorporated by reference in the entirety for the use of understanding such FET arrays.

FIG. 4 shows a cross-section of a biosensor 400 that can be used in various embodiments. Biosensor 400 has wells 406, 408, 410, 412, and 414 that can each hold more than one cluster during a base calling cycle (e.g., 2 clusters per well). The sample surface 334 may be substantially planar as shown in FIG. 3. However, in alternative embodiments, the sample surface 334 may be shaped to define wells (or reaction chambers) in which each well has one or more reaction sites. The wells may be defined by, for example, well walls that effectively separate the reaction site(s) of one well from the reaction site(s) of an adjacent well.

As shown in FIG. 4, the wells 406, 408, 410, 412, and 414 may be distributed in a pattern along the sample surface 334. For example, the wells 406, 408, 410, 412, and 414 may be located in rows and columns along the sample surface 334 in a manner that is similar to a microarray. However, it is understood that various patterns of wells 406, 408, 410, 412, and 414 may be used. In particular embodiments, each of the wells 406, 408, 410, 412, and 414 includes more than one cluster of biomolecules (e.g., oligonucleotides) that are immobilized on the sample surface 334. For example, well 406 holds cluster pair 306AB, well 408 holds cluster pair 308AB, well 410 holds cluster pair 310AB, well 412 holds cluster pair 312AB, and well 414 holds cluster pair 314AB.

The sensors are configured to detect light signals that are emitted from within the wells. In particular embodiments, pixel areas 306', 308', 310', 312', and 314' can be also associated with corresponding wells 406, 408, 410, 412, and 414 on the sample surface 334, such that light emitted from the wells 406, 408, 410, 412, and 414 is received by the associated pixel areas 306', 308', 310', 312', and 314' and captured by the corresponding sensors 306, 308, 310, 312, and 314.

In embodiments, the sample surface 334 has a fixed position relative to the sampling device 304 so that the wells 406, 408, 410, 412, and 414 have known spatial locations relative to at least one predetermined sensor (or pixel). The at least one predetermined sensor detects activity of the desired reactions from the overlying well. As such, the wells 406, 408, 410, 412, and 414 may be assigned to at least one of the sensors 306, 308, 310, 312, and 314. To this end, the circuitry of the sampling device 304 may include kernels that automatically associate pixel signals (or detection signals) provided by predetermined sensors 306, 308, 310, 312, and 314 with the assigned wells 406, 408, 410, 412, and 414. By way of example, when pixel signals are generated by sensor 306 shown in FIG. 4, the pixel signals will automatically be associated with the well 406 shown in FIG. 4. Such a configuration may facilitate processing and analyzing the detection data. For instance, the pixel signals from one well may automatically be located at a certain position on the array based on row-wise and/or column-wise decoding.

In some embodiments, the sensors (or pixels) are underlying or below the clusters. In other embodiments, the sensors (or pixels) are overlying or on top of the clusters. In yet other embodiments, the sensors (or pixels) are to the side of the clusters (e.g., to the right and/or left).

Multiple Cluster Base Call Per Sensor (or Pixel)

In embodiments, the technology disclosed increases throughput of the biosensor 300 by using pixel signals from fewer sensors (or pixels) than a number of clusters base called in a base calling cycle. In particular embodiments, if the biosensor 300 has N active sensors, then the technology disclosed uses pixel signals from the N active sensors to base call N+M clusters, where M is a positive integer. In embodiments, this is achieved by base calling multiple clusters per sensor (or pixel), as described below.

In embodiments, a sensor (or pixel) on the sample surface 334 is configured to receive light emissions from at least two clusters. In some embodiments, the sensor simultaneously receives the light emissions from the at least two clusters.

In particular embodiments, the intensity of respective light emissions of the two clusters is significantly different such that one of the two clusters is a "bright" cluster and the other is a "dim" cluster. In embodiments, the intensity values vary between base calling cycles and thus the classification of bright and dim can also change between cycles. In other embodiments, a bright cluster is referred to as a "major" or "dominant" cluster and a dim cluster is referred to as a "minor" or "subordinate" cluster. Some examples of intensity value ratios of emissions between bright and dim clusters include 0.55:0.45, 0.60:0.40, 0.65:0.35, 0.70:0.30, 0.75:0.25, 0.80:0.20, 0.85:0.15, 0.90:0.10, and 0.95:0.05.

In yet other embodiments, the at least two clusters are not bright and dim clusters, but instead clusters with different intensities or clusters generating different types of signals.

During each sampling event (e.g., each illumination stage or each image acquisition stage), signal processor 138 receives a common, single pixel signal for at least two clusters (e.g., both the bright and dim clusters). The common, single pixel generated at each sampling event includes/represents/reflects/carries light emissions/intensity signals/light captured/sensed information for or from the at least two clusters (e.g., both the bright and dim clusters). In other words, the at least two clusters (e.g., both the bright and dim clusters) contribute to the common, single pixel generated at each sampling event. Accordingly, light emissions from the at least two clusters (e.g., both the bright and dim clusters) are detected simultaneously at each sampling event and the common, single pixel reflects light emissions from the at least two clusters (e.g., both the bright and dim clusters).

For example, in FIGS. 3 and 4, cluster pair 306AB includes two clusters 306A and 306B which share a sensor 306. As such, cluster 306A can be the dim cluster and cluster 306B can be the bright cluster, depending on their respective intensity values. Signal processor 138 then uses a base calling algorithm to classify pixel signals from the bright and dim clusters into one of sixteen distributions, as described below. In particular embodiments, the bright and dim cluster co-occupy a well, such as well 406. Thus, cluster pairing can be defined based on a shared pixel area or a shared well, or both.

FIGS. 5A and 5B are scatter plots 500A and 500B that depict base calling of the bright and dim clusters using their respective pixel signals detected by the shared sensor in accordance with one embodiment. X-axis of the scatter plots 500A and 500B represents the AT pixel signals detected during a second illumination stage of the sampling event which induces illumination from a given cluster indicating nucleotide bases A and T. Y-axis of the scatter plots 500A and 500B represents the CT pixel signals detected during a first illumination stage of a sampling event which induces illumination from a given cluster indicating nucleotide bases C and T.

Scatter plot 500A shows four distributions 502, 504, 506, and 508 to which signal processor 138 classifies pixel signals from the bright cluster. In the illustrated embodiment, distribution 502 represents nucleotide base C in the bright cluster, distribution 504 represents nucleotide base T in the bright cluster, distribution 506 represents nucleotide base G in the bright cluster, and distribution 508 represents nucleotide base A in the bright cluster.

Scatter plot 500B shows sixteen sub-distributions (or distributions) 502A-D, 504A-D, 506A-D, and 508A-D, with four sub-distributions for each of the four distributions 502, 504, 506, and 508 of the scatter plot 500A), to which signal processor 138 classifies pixel signals from the dim cluster. In the illustrated embodiment, sub-distributions annotated with letter "A" represent nucleotide base C in the dim cluster, sub-distributions annotated with letter "B" represent nucleotide base T in the dim cluster, sub-distributions annotated with letter "C" represent nucleotide base G in the dim cluster, and sub-distributions annotated with letter "D" represent nucleotide base A in the dim cluster. In other embodiments, different encodings of the bases may be used. When the signal processor classifies pixel signals from a dim cluster in one of the sixteen sub-distributions, the classification of the corresponding bright cluster is determined by the distribution which includes the dim cluster's sub-distribution. For example, if a dim cluster is classified to sub-distribution 508B (nucleotide base T), then the distribution for the corresponding bright cluster is 508 (nucleotide base A). As a result, the signal processor 138 base calls the bright cluster as A and the dim cluster as T.

FIG. 6 is a scatter plot 600 that depicts sixteen distributions (or bins) produced by intensity values from bright and dim clusters of a cluster pair in accordance with one embodiment. In embodiments, the sixteen bins are produced over a plurality of base calling cycles. Signal processor 138 combines pixel signals from the bright and dim clusters and maps them into one of the sixteen bins. When the combined pixel signals are mapped to bin 612 for a base calling cycle, the signal processor 138 base calls the bright cluster as C and the dim cluster as C. When the combined pixel signals are mapped to bin 614 for the base calling cycle, the signal processor 138 base calls the bright cluster as C and the dim cluster as T. When the combined pixel signals are mapped to bin 616 for the base calling cycle, the signal processor 138 base calls the bright cluster as C and the dim cluster as G. When the combined pixel signals are mapped to bin 618 for the base calling cycle, the signal processor 138 base calls the bright cluster as C and the dim cluster as A.

When the combined pixel signals are mapped to bin 622 for the base calling cycle, the signal processor 138 base calls the bright cluster as T and the dim cluster as C. When the combined pixel signals are mapped to bin 624 for the base calling cycle, the signal processor 138 base calls the bright cluster as T and the dim cluster as T. When the combined pixel signals are mapped to bin 626 for the base calling cycle, the signal processor 138 base calls the bright cluster as T and the dim cluster as G. When the combined pixel signals are mapped to bin 628 for the base calling cycle, the signal processor 138 base calls the bright cluster as T and the dim cluster as A.

When the combined pixel signals are mapped to bin 632 for the base calling cycle, the signal processor 138 base calls the bright cluster as G and the dim cluster as C. When the combined pixel signals are mapped to bin 634 for the base calling cycle, the signal processor 138 base calls the bright cluster as G and the dim cluster as T. When the combined pixel signals are mapped to bin 636 for the base calling cycle, the signal processor 138 base calls the bright cluster as G and the dim cluster as G. When the combined pixel signals are mapped to bin 638 for the base calling cycle, the signal processor 138 base calls the bright cluster as G and the dim cluster as A.

When the combined pixel signals are mapped to bin 642 for the base calling cycle, the signal processor 138 base calls the bright cluster as A and the dim cluster as C. When the combined pixel signals are mapped to bin 644 for the base calling cycle, the signal processor 138 base calls the bright cluster as A and the dim cluster as T. When the combined pixel signals are mapped to bin 646 for the base calling cycle, the signal processor 138 base calls the bright cluster as A and the dim cluster as G. When the combined pixel signals are mapped to bin 648 for the base calling cycle, the signal processor 138 base calls the bright cluster as A and the dim cluster as A.

FIG. 7A is a detection table 700A that illustrates a base calling scheme for one dye and two illumination stage sequencing protocol in accordance with one embodiment. One avenue of differentiating between the different strategies for detecting nucleotide incorporation in a sequencing reaction using one fluorescent dye (or two or more dyes of same or similar excitation/emission spectra) is by characterizing the incorporations in terms of the presence or relative absence, or levels in between, of fluorescence transition that occurs during a sequencing cycle. As such, sequencing strategies can be exemplified by their fluorescent profile for a sequencing cycle. For strategies disclosed herein, "1" and "0" denotes a fluorescent state in which a nucleotide is in a signal state (e.g., detectable by fluorescence) or whether a nucleotide is in a dark state (e.g., not detected or minimally detected at an imaging step). A "0" state does not necessarily refer to a total lack, or absence of signal. Minimal or diminished fluorescence signal (e.g., background signal) is also contemplated to be included in the scope of a "0" state as long as a change in fluorescence from the first to the second illumination event (or vice versa) can be reliably distinguished. In one embodiment, an exemplary strategy for detecting and determining nucleotide incorporation in a sequencing reaction using one fluorescent dye (or two dyes of same or similar excitation/emission spectra) and two illumination events is exemplified by the detection table 700A.

In the illustrated embodiment, during the first illumination stage (AT signal), nucleotide base A is labeled or on (depicted by bit 1), nucleotide base C is unlabeled or off (depicted by bit 0), nucleotide base G is unlabeled or off (depicted by bit 0), and nucleotide base T is labeled or on (depicted by bit 1). During the second illumination stage (CT signal), nucleotide base A is unlabeled or off (depicted by bit 0), nucleotide base C is labeled or on (depicted by bit 1), nucleotide base G is unlabeled or off (depicted by bit 0), and nucleotide base T is labeled or on (depicted by bit 1).

FIG. 7B is a base calling table 700B that shows a classification scheme for classifying combined pixel signals, each pixel signal including information from the bright and dim clusters of a cluster pair, into one of sixteen bins in accordance with one embodiment.

The technology disclosed generates a pixel signal that represents information sensed from all of the multiple clusters in a pixel area of a shared sensor. A sequence of such pan-cluster pixel signals is then mapped to bins to base call all the clusters. Thus, a separate, discrete pixel signal for each cluster is not generated. This has the advantage of multifold reduction in image acquisition and thereby reducing sequencing time and accelerating sequence processing.

Consider FIG. 7B in which a bright cluster and a dim cluster in a pixel area are base called. At each cycle, two pixels signals are sampled: an AT signal and a CT signal. During the first sampling event, light emissions from both the bright and dim clusters for fluorescently labeled adenines (A) and thymines (T) are recorded in the AT signal, as opposed to two separate AT signals, i.e., one for the bright cluster and another for the dim cluster. Similarly, during the second sampling event, light emissions from both the bright and dim clusters for fluorescently labeled cytosines (C) and thymines (T) are recorded in the CT signal, as opposed to two separate CT signals, i.e., one for the bright cluster and another for the dim cluster.

This way, light emissions from both clusters are received during a single sampling event and yield a common, single pixel signal. Therefore, for each sampling event, emissions from both the bright and dim clusters are jointly represented in a common, single pixel signal.

Furthermore, a common, single sequence of pixel signals is used to jointly base call both the bright and dim clusters at each cycle. In FIG. 7B, the AT and CT signals together form the common, single sequence of pixel signals. Thus, the technology disclosed does not use two separate sequences of pixel signals, i.e., one for the bright cluster and another for the dim cluster, to separately base call the bright and dim clusters. This has the advantage of multifold reduction in signal processing and thereby reducing sequencing time and accelerating sequence processing.

The disclosed base calling involves mapping the common, single sequence of pixel signals to bins. For instance, in FIG. 7B, with values 1 and 0, the sequence of AT and CT signals is mapped to bin 1 and the bright and dim clusters are assigned base calls A and A, respectively.

In the example shown in FIG. 7B, a deterministic bright to dim cluster intensity ratio of 0.7:0.3 is used. In embodiments, the intensity ratio is undetermined, as such, it produces detectable bright and dim clusters that share a pixel area or share a well, or both.

As a result of the intensity ratio being 0.7:0.3 (i.e., intensity values of light emissions from the bright and dim clusters being significantly different), the pixel signals readout from the shared sensor during the two illumination stages over a plurality of base calling cycles produces sixteen bins 701 (bins 1-16). Each bin has a unique pair of pixel signal values (e.g., unique pair 710 for bin 1), the pair comprises a first pixel signal value 706 for the two clusters in the first illumination stage (AT signal) and a second pixel signal value 708 for the two clusters in the second illumination stage (CT signal).

Each pixel signal value 706 or 708 is in turn composed of two signal portions 706A and 706B or 708A and 708B, which are additively combined to produce the corresponding pixel signal values 706 or 708. Thus, a common, single pixel signal is generated both the bright and dim clusters.

For each pixel signal value 706 or 708, a first signal portion 706A or 708A is determined from the intensity value of light emissions by the first cluster and a second signal portion 706B or 708B is determined from the intensity value of light emissions by the second cluster. In the example shown in base calling table 700B, the first cluster is the bright cluster 702 and the second cluster is the dim cluster 704.

Since the intensity ratio is 0.7:0.3, the first and second pixel signals can take one of the four possible values—1, 0, 0.7, or 0.3. Additionally, when the bright cluster produces an "on" bit, its contribution or signal portion (706A, 708A) is 0.7. In contrast, when the dim cluster produces an "on" bit, its contribution or signal portion (706B, 708B) is 0.3. A contribution or signal portion representing an "off" bit is identified by 0 for both the clusters. Sixteen unique combinations of the four possible values 1, 0, 0.7, and 0.3 produce the sixteen bins 701.

Once the sixteen bins 701 are identified by the signal processor 138 for a bright-dim cluster pair overlying a shared sensor or well over a plurality of base calling cycles, the signal processor 138 uses the base calling table 700B to base call the bright and dim cluster in successive base calling cycles. In one embodiment, the identification results in classification of the well as holding more than one cluster (i.e., the bright cluster and the dim cluster). Thus, in a successive base calling cycle, the signal processor performs a first pixel readout of the shared sensor for the first illumination stage (AT signal). This first pixel readout produces a first pixel signal. Similarly, a second pixel readout for the second illumination stage (CT signal) produces a second pixel signal. The first and second pixel signals produce intensity values that are combined to form a value pair. This value pair can be compared against one of the sixteen unique value pairs in the base calling table 700B. Based on the comparison, one of the sixteen bins is selected. Base call for the bright and dim clusters is made in accordance with the nucleotide bases assigned to the selected bin. This process is repeated for subsequent base calling cycles to identify nucleotide bases present in the respective nucleotide sequences of the bright and dim cluster.

Therefore, the technology disclosed treats emissions from all the clusters as useful for base calling, irrespective of their relative strength. This is because the clusters that have weaker emissions (e.g., dim cluster) are not separately base called; instead they are jointly base called with clusters that have stronger emissions (e.g., bright cluster) using a common, single sequence of pixel signals carrying both the stronger and weaker emissions.

As discussed above, the shared sensor captures photons from two different clusters (e.g., a bright cluster and a dim cluster). In some embodiments, the signal portions are detected by deconvoluting the signal readings from the shared sensor to distinguish the individual signal portions generated by each of the clusters.

FIG. 8 shows a method 800 of base calling by analyzing pixel signals emitted by a plurality of clusters that share a pixel area in accordance with one embodiment. At action 802, a first pixel signal that represents light gathered from multiple clusters in a first pixel area during a first illumination stage of the base calling cycle is detected. In some embodiments, the first pixel area receives light from an associated well on the sample surface 334. In other embodiments, the first pixel area receives light from more than one associated well on the sample surface 334.

At action 804, a second pixel signal that represents light gathered from multiple clusters in the first pixel area during a second illumination stage of the base calling cycle is detected.

In embodiments, the first pixel area underlies a plurality of clusters that shares the first pixel area. The first and second pixel signals can be gathered by a first sensor from the first pixel area. The first and second pixel signals can be detected by the signal processor 138, which is configured for processing pixel signals gathered by the first sensor.

In some embodiments, the first illumination stage can induce illumination from the first and second clusters to produce emissions from labeled nucleotide bases A and T, and the second illumination stage can induce illumination from the first and second clusters to produce emissions from labeled nucleotide bases C and T.

At action 806, a combination of the first and second pixel signals is used to identify nucleotide bases incorporated onto each cluster of the plurality of clusters during the base calling cycle. In embodiments, this includes mapping the first pixel signal into at least four bins and mapping the second pixel signal into at least four bins, and combining the mapping of the first and second pixel signals for the base calling.

In embodiments, method 800 is applied to identify the nucleotide bases incorporated onto the plurality of clusters at a plurality of pixel areas during the base calling cycle. In embodiments, method 800 is repeated over successive base calling cycles to identify the nucleotide bases incorporated onto the plurality of clusters at the plurality of pixel areas during each of the base calling cycles.

In some embodiments, for each of the base calling cycles, the first and second pixel signals emitted by the plurality of clusters at the plurality of pixel areas are detected and stored. After the base calling cycles, the combination of the first and second pixel signals is used to identify the nucleotide bases incorporated onto the plurality of clusters at the plurality of pixel areas during each of the previous base calling cycles.

FIG. 9 depicts a method 900 of identifying pixel areas with more than one cluster on the sample surface 334 of the biosensor 300 and base calling clusters at the identified pixel areas in accordance with one embodiment. At action 902, a plurality of base calling cycles is performed. Each base calling cycle has a first illumination stage and a second illumination stage.

At action 904, a sensor associated with a pixel area of the sample surface 334 captures—(a) a first set of intensity values generated during the first illumination stage of the base calling cycles and (b) a second set of intensity values generated during the second illumination stage of the base calling cycles. In embodiments, the intensity values are normalized. Also, in some embodiments, the pixel area receives light from an associated well on the sample surface 334.

At action 906, the signal processor 138 fits (shown in FIG. 6) to the first and second sets of intensity values to a one of a set of distributions (where a distribution is a area in the two dimensional plot of FIG. 6), including sixteen distributions in this example. and, based on the fitting, classifies the pixel area as having more than one cluster. In embodiments, the signal processor 138 uses one or more algorithms for fitting the sixteen distributions. Examples of algorithms include k-means clustering algorithm, k-means-like clustering algorithm, expectation maximization algorithm, and histogram based algorithm.

At action 908, for a successive base calling cycle, the signal processor 138 detects the first and second sets of intensity values for a cluster group at the pixel area. At action 910, the signal processor 138 selects a distribution for the cluster group from among the sixteen distributions. The distribution identifies a nucleotide base present in each cluster of the cluster group.

In some embodiments, the intensity ratios are an inherent property of the bright and dim clusters that produce significantly different light emissions. In other embodiments, the intensity ratios and the significantly different light emissions between clusters are actuated by the following embodiments, such as uneven distribution of clusters on a flat surface, dual wells per sensor (or pixel), and off-axis illumination.

Flat Surface-Based Spatial Analysis of Unevenly Distributed Clusters

FIG. 10 illustrates a top plan view 1000 of the sample surface 334 having pixel areas (depicted as rectangles) on which a plurality of clusters (depicted as circles) are unevenly distributed in accordance with one embodiment. Positions of the clusters on the surface well 334 may not be confined by wells relative to the locations of the sensors (or pixels). Such arrangement of clusters on the sample surface 334 is referred to as uneven distribution. In particular embodiments, the clusters are unevenly distributed on a "flat" configuration of the sample surface 334 that does not include wells. In such a flat surface embodiment, the pixel areas can overlap.

In the illustrated embodiment, consider two example clusters 1002 and 1004 that share four pixel areas A, B, C, and D. Depending on the cluster's relative position with respect to centers of the pixel areas A, B, C, and D, the corresponding sensors (or pixels) receive different amount of light emissions. This produces illumination patterns that create differential crosstalk between the clusters 1002 and 1004 over a plurality of base calling cycles of a sequencing run, which can be used to construct a map of cluster locations on the sample surface 334, as described below. The differential crosstalk is embodied in the pixel signals as information from two or more clusters in one pixel signal.

Signal processor 138 executes time sequence and spatial analysis of a plurality of sequences of pixel signals for the clusters to detect patterns of illumination corresponding to individual clusters unevenly distributed on the sample surface 334. The plurality of sequences of pixel signals encodes differential crosstalk between at least two clusters resulting from their uneven distribution over the pixel areas.

Spatial analysis includes using the sequences of pixel signals gathered from a group of pixel areas to determine spatial characteristics of a given cluster, including location of the given cluster on the sample surface 334. After the cluster locations and their illumination patterns are identified over the plurality of base calling cycles, the clusters can be base called by the signal processor 138 using one of the sequencing protocols discussed above.

In the spatial analysis embodiment, the technology disclosed increases throughput of the biosensor 300 by using N sensors (or pixels) to locate and base call N+M unevenly distributed clusters on the sample surface 334, where M is a positive integer. In some embodiments, M is equal to N or almost equal to N. In other embodiments, when two clusters, which share (or co-occupy) a pixel area and/or well, are not separately detectable due to inadequate difference in intensity values, M might not be equal to N or even be less than N.

Dual Wells Per Sensor (or Pixel)

FIG. 11A illustrates a side view 1100A of a sample surface having two wells per pixel area including a dominant (or major) well and a subordinate (or minor) well in accordance with one embodiment. FIG. 11B depicts a top plan view 1100B of the sample surface of FIG. 11A.

In the illustrated embodiment, shared sensor 1106 (or pixel) corresponds to two wells 1102 and 1104 on the sample surface 334. The dominant well has a larger cross section over the pixel area than the subordinate well. Well 1104 is the dominant well and well 1102 is the subordinate well because well 1104 has a larger cross section over the sensor 1106.

In embodiments, the two wells have different offsets relative to a center of the pixel area 1106'. In the illustrated embodiment, dominant well 1104 is more proximate to the pixel area center 1106A than the subordinate well 1102 (i.e., dominant well 1104 has a smaller offset relative to the pixel area center 1106A than the subordinate well 1102).

Due to the differential cross section coverage and relative offsets result, the sensor 1106 receives different amounts of illumination from the two wells during illumination stages of the base calling cycle (or sampling event). Since each of the wells 1102 and 1104 holds a corresponding cluster 1102A and 1104A, the different amounts of illumination allow for identification of one of the clusters as bright (or major) and the other as dim (or minor). In the illustrated embodiment, cluster 1102A within the dominant well 1102 is identified as the bright cluster and cluster 1104A within the subordinate well 1104 is identified as the dim cluster. In embodiments, sensor 1106 receives an amount of illumination from the bright cluster 1102A that is greater than an amount of illumination received from the dim cluster 1104A in the subordinate well 1104.

After the bright and dim clusters are identified, they can be base called by the signal processor 138 using one of the sequencing protocols discussed above. In some dual well per sensor (or pixel) embodiments, the technology disclosed increases throughput of the biosensor 300 by base calling two clusters 1102A and 1102B held by two corresponding wells 1102 and 1104 using one shared sensor 1106. In other dual well per sensor (or pixel) embodiments, the technology disclosed increases throughput of the biosensor 300 by using N sensors to base call N+M clusters on corresponding N+M wells of the sample surface 334, where M is a positive integer. In some embodiments, M is equal to N or almost equal to N. In other embodiments, M might not be equal to N or even be less than N.

Off-Axis Illumination

FIGS. 12A and 12B show off-axis illumination 1200A and 1200B of a well overlying a pixel area of a sample surface. Illumination system 109 is configured to illuminate the pixel areas 1204' and 1214' (associated with sensors 1204 and 1214) with different angles of illumination signals 1201 and 1211 during illumination stages of a base calling cycle. As a result, wells 1202 and 1212 are illuminated with off-axis or non-orthogonal illumination signals. This produces asymmetrically illuminated well regions in each of the wells 1202 and 1212, depicted in FIGS. 12A and 12B with light and dark shaded areas in each well. The asymmetrically illuminated well regions of a well include at least a dominant well region 1202B' or 1212A' (depicted in lighter shade) and a subordinate well region 1202A' or 1212 B' (depicted in darker shade), such that during the base calling cycle the dominant well region is illuminated more than the subordinate well region.

Each well is configured to hold more than one cluster during the base calling cycle, with the dominant and subordinate well regions each including a cluster. In the illustrated embodiment, well 1202 holds two clusters 1202A and 1202B, with cluster 1202A within the subordinate well region 1202A' and cluster 1202B within the dominant well region 1202B'. Well 1212 holds two clusters 1212A and 1212B, with cluster 1212A within the dominant well region 1212A' and cluster 1212B within the subordinate well region 1202B'.

Due to the off-axis illumination, pixel areas 1204' and 1214' of the wells 1202 and 1212 receive different amounts of illumination from dominant and subordinate regions of a well. As a result, during the base calling cycle, clusters in the dominant well regions produce greater amounts of illumination than clusters in the subordinate well regions. For each well, this allows for identification of one of the clusters as bright (or major) and the other as dim (or minor). In the illustrated embodiment, for well 1202, cluster 1202B within the dominant well region 1202B' is identified as the bright cluster and cluster 1202A within the subordinate well region 1202A' is identified as the dim cluster. For well 1212, cluster 1212A within the dominant well region 1212A' is identified as the bright cluster and cluster 1212B within the subordinate well region 1212B' is identified as the dim cluster.

After the bright and dim clusters are identified for each well, they can be base called by the signal processor 138 using one of the sequencing protocols discussed above. In the off-axis illumination embodiment, the technology disclosed increases throughput of the biosensor 300 by using N sensors (or pixels) to base call N+M clusters within N non-orthogonally illuminated wells on the sample surface 334, where M is a positive integer. In some embodiments, M is equal to N or almost equal to N. In other embodiments, when two clusters, which share (or co-occupy) a pixel area and/or well, are not separately detectable due to inadequate difference in intensity values, M might not be equal to N or even be less than N.

In one embodiment, the off-axis illumination is at a forty-five degree angle. In some embodiments, one well overlies per pixel area. In other embodiments, two wells overlie per pixel area.

FIG. 12C illustrates asymmetrically illuminated well regions 1200C produced by the off-axis illumination of FIGS. 12A and 12B in accordance with one embodiment. As shown in FIG. 12C, well region 1220 is more illuminated than well region 1230.

CLAUSES

The disclosure also includes the following clauses:

1. A device for base calling, comprising:
   a receptacle and a biosensor, the receptacle holding the biosensor, the biosensor having
   a sample surface that holds a plurality of clusters during a sequence of sampling events,
   an array of sensors configured to generate a plurality of sequences of pixel signals, the array having a number N of active sensors, the sensors in the array disposed relative to the sample surface to generate respective pixel signals during the sequence of sampling events from the number N of corresponding pixel areas of the sample surface to produce the plurality of sequences of pixel signals, and a communication port which outputs the plurality of sequences of pixel signals; and
   a signal processor coupled to the receptacle, and configured to receive and to process the plurality of sequences of pixel signals to classify results of the sequence of sampling events on clusters in the plurality of clusters, including using the plurality of sequences of pixel signals to classify results of the sequence of sampling events on a number N+M of clusters in the plurality of clusters from the number N of active sensors, where M is a positive integer.
2. The device of clause 1, wherein the results of the sequence of sampling events correspond to nucleotide bases in the clusters.
3. The device of clause 1 or clause 2, wherein the sampling events comprise two illumination stages in time sequence, and sequences of pixel signals in the plurality of sequences of pixel signals include a set of signal samples for each sampling event, the set including at least one pixel signal from each of the two illumination stages.
4. The device of clause 3, wherein the signal processor includes logic to classify results for two clusters from the sequences of pixel signals from a single sensor in the array of sensors.
5. The device of clause 4, wherein the logic to classify results for two clusters includes mapping a first pixel signal of the set of signal samples for a sampling event from a particular sensor into at least four bins, and mapping a second pixel signal of the set of signal samples for the sampling event into at least four bins, and logically combining the mapping of the first and second pixel signals to classify the results for two clusters.
6. The device of any one of clauses 1 to 5, wherein the sensors in the array of sensors comprise light detectors.
7. The device of any one of clauses 1 to 6, wherein the sampling events comprise two illumination stages in time sequence, and sequences of pixel signals in the plurality of sequences of pixel signals include a set of signal samples for each sampling event, the set including at least one pixel signal from each of the two illumination stages, and wherein the first illumination stage induces illumination from a given cluster indicating nucleotide bases A and T and the second illumination stage induces illumination from a given cluster indicating nucleotide bases C and T, and said classifying results comprises calling one of the nucleotide bases A, C, T or G.
8. The device of any one of clauses 1 to 7, wherein the sample surface holds clusters that are distributed unevenly over the pixel areas, and the signal processor executes time sequence and spatial analysis of the plurality of sequences of pixel signals to detect patterns of illumination corresponding to individual clusters on the sample surface, and to classify the results of the sampling events for the individual clusters, wherein the plurality of sequences of pixel signals encodes differential crosstalk between at least two clusters resulting from their uneven distribution over the pixel areas.
9. The device of any one of clauses 1 to 8, wherein the sample surface comprises an array of wells overlying the pixel areas, including two wells per pixel area, the two wells per pixel area including a dominant well and a subordinate well, the dominant well having a larger cross section over the pixel area than the subordinate well.
10. The device of any one of clauses 1 to 9, wherein the sample surface comprises an array of wells overlying the pixel areas, and the sampling events include at least one chemical stage with a number K of illumination stages where K is a positive integer, where the illumination stages of the K illumination stages illuminate the pixel areas with different angles of illumination, and the sequences of pixel signals include a set of signal samples for each sampling event, the set including the number K of pixel signals for the at least one chemical stage of the sampling events.
11. The device of any one of clauses 1 to 10, wherein the sample surface comprises an array of wells overlying the pixel areas, and the sampling events include a first chemical stage with a number K of illumination stages where K is a positive integer, where the illumination stages of the K illumination stages illuminate the pixel areas with different angles of illumination, and a second chemical stage with a number J of illumination stages where J is a positive integer, where the illumination stages of the K illumination stages in the first chemical stage and of the J illumination stages in the second chemical stage illuminate the wells in the array of wells with different angles of illumination, and the sequences of pixel signals include a set of signal samples for each sampling event, the set including the number K of pixel signals for the first chemical stage plus the number J of pixel signals for the second chemical stage of the sampling events.

12. A biosensor for base calling, comprising:

a sampling device, the sampling device including a sample surface having an array of pixel areas and a solid-state imager having an array of sensors, each sensor generating pixel signals in each base calling cycle, each pixel signal representing light gathered from a corresponding pixel area of the sample surface; and a signal processor configured for connection to the sampling device that receives and processes the pixel signals from the sensors for base calling in a base calling cycle, and uses the pixel signals from fewer sensors than a number of clusters base called in the base calling cycle.

13. The biosensor of clause 12, wherein a pixel area receives light from a well on the sample surface and the well is configured to hold more than one cluster during the base calling cycle.

14. The biosensor of clause 13, wherein a cluster comprises a plurality of single-stranded deoxyribonucleic acid (abbreviated DNA) fragments having an identical nucleic acid sequence.

15. A computer-implemented method of base calling, including:

for a base calling cycle of a sequencing by synthesis (abbreviated SBS) run, receiving from a communication port a plurality of sequences of pixel signals, the plurality of sequences of pixel signals being generated by an array of sensors, the array having a number N of active sensors, the sensors in the array disposed relative to the sample surface to generate respective pixel signals during the sequence of sampling events from the number N of corresponding pixel areas of the sample surface to produce the plurality of sequences of pixel signals; and processing the plurality of sequences of pixel signals to classify results of the sequence of sampling events on clusters in the plurality of clusters, including using the plurality of sequences of pixel signals to classify results of the sequence of sampling events on clusters in the plurality of clusters, including using the plurality of sequences of pixel signals to classify results of the sequence of sampling events on a number N+M of clusters in the plurality of clusters from the number N of active sensors, where M is a positive integer.

16. The method of clause 15, further including:

mapping a first pixel signal, which represents light gathered from a first pixel area during a first illumination stage of the base calling cycle, into at least four bins and mapping a second pixel signal, which represents light gathered from the first pixel area during a second illumination stage of the base calling cycle, into at least four bins, and combining the mapping of the first and second pixel signals to identify the incorporated nucleotide bases.

17. The method of clause 15 or clause 16, further including applying the method to identify the nucleotide bases incorporated onto the plurality of clusters at a plurality of pixel areas during the base calling cycle.

18. The method of clause 17, further including repeating the method over successive base calling cycles to identify the nucleotide bases incorporated onto the plurality of clusters at the plurality of pixel areas during each of the base calling cycles.

19. The method of clause 18, further including:

for each of the base calling cycles, detecting and storing the first and second pixel signals emitted by the plurality of clusters at the plurality of pixel areas, and after the base calling cycles, using the combination of the first and second pixel signals to identify the nucleotide bases incorporated onto the plurality of clusters at the plurality of pixel areas during each of the previous base calling cycles.

20. The method of any one of clauses 16 to 19, wherein the first pixel area receives light from an associated well on a sample surface.

21. The method of clause 20, wherein the first pixel area receives light from more than one associated well on the sample surface.

22. The method of any one of clauses 16 to 21, wherein the first and second pixel signals are gathered by a first sensor from the first pixel area.

23. The method of clause 22, wherein the first and second pixel signals are detected by a signal processor configured for processing pixel signals gathered by the first sensor.

24. The method of any one of clauses 15 to 23, wherein the first illumination stage induces illumination from the first and second clusters to produce emissions from labeled nucleotide bases A and T and the second illumination stage induces illumination from the first and second clusters to produce emissions from labeled nucleotide bases C and T.

25. The method of any one of clauses 15 to 24, in which said base calling includes using a device as defined in any one of clauses 1 to 11.

26. A method of identifying pixel areas with more than one cluster on a sample surface of a biosensor and base calling clusters at the identified pixel areas, including:

performing a plurality of base calling cycles, each base calling cycle having a first illumination stage and a second illumination stage;

capturing at a sensor associated with a pixel area of the sample surface, a first set of intensity values generated during the first illumination stage of the base calling cycles, and a second set of intensity values generated during the second illumination stage of the base calling cycles;

fitting sixteen distributions to the first and second sets of intensity values using a signal processor and, based on the fitting, classifying the pixel area as having more than one cluster; and for a successive base calling cycle, detecting the first and second sets of intensity values for a cluster group at the pixel area using the signal processor, and selecting a distribution for the cluster group, wherein the distribution identifies a nucleotide base present in each cluster of the cluster group.

27. The method of clause 26, wherein the fitting comprises using one or more algorithms, including a k-means clustering algorithm, a k-means-like clustering algorithm, an expectation maximization algorithm, and a histogram based algorithm.

28. The method of clause 26 or clause 27, further including normalizing the intensity values.

29. The method of any one of clauses 26 to 28, wherein the pixel area receives light from an associated well on the sample surface.

30. The method of any one of clauses 26 to 29, in which said identifying and base calling includes using a device as defined in any one of clauses 1 to 11 or a biosensor as defined in any one of clauses 12 to 14.

31. A computer-implemented method of base calling, comprising:

providing a first pixel signal that represents light gathered from a first pixel area during a first illumination stage of a base calling cycle of a sequencing by synthesis (abbreviated SBS) run and a second pixel signal that represents light gathered from said first pixel area during a second illumination stage of said base calling cycle of said SBS run, wherein the first pixel area underlies first and second clusters that share the first pixel area;

providing a signal processor configured for processing at least said first and second pixel signals;

mapping the first pixel signal into at least four bins and mapping the second pixel signal into at least four bins using said signal processor; and logically combining the mapping of the first and second pixel signals to identify the nucleotide base incorporated onto each of said first and second clusters during said base calling cycle.

32. A computer-implemented method of identifying pixel areas with more than one cluster on a sample surface of a biosensor and base calling clusters at the identified pixel areas, comprising:

providing a first set of intensity values generated during a first illumination stage of a base calling cycle and a second set of intensity values generated during a second illumination stage of the base calling cycle, wherein the first and second sets of intensity values represent the intensity of light gathered at a sensor associated with a pixel area of the sample surface;

fitting sixteen distributions to the first and second sets of intensity values using a signal processor and, based on the fitting, classifying the pixel area as having more than one cluster; and for a successive base calling cycle, providing first and second sets of intensity values for a cluster group at the pixel area using the signal processor, and selecting a distribution for the cluster group, wherein the distribution identifies a nucleotide base present in each cluster of the cluster group.

33. The computer-implemented method of clause 32, wherein the fitting comprises using one or more algorithms, including a k-means clustering algorithm, a k-means-like clustering algorithm, an expectation maximization algorithm, and a histogram based algorithm.

34. A device for base calling, comprising:

a receptacle and a biosensor, the receptacle holding the biosensor, the biosensor having a sample surface configured to hold a plurality of clusters during a sequence of sampling events, the sample surface comprising a number N of pixel areas, and the sampling events comprising two illumination stages in time sequence, an array of sensors comprising light detectors configured to generate a plurality of sequences of pixel signals including at least one pixel signal for each pixel area and illumination stage, the array having a number N of active sensors each associated with a corresponding pixel area of the N pixel areas and configured to detect light emissions gathered from the associated pixel area, to generate respective pixel signals during the sequence of sampling events representing the light emissions gathered from the corresponding pixel area to produce the plurality of sequences of pixel signals, wherein the sample surface is configured such that at least one active sensor detects light emissions from at least two clusters forming a cluster pair of the plurality of clusters, wherein the intensity of respective light emissions of the two clusters is significantly different, and a communication port which outputs the plurality of sequences of pixel signals; and a signal processor coupled to the receptacle, and configured to receive and to process the plurality of sequences of pixel signals to classify results of the sequence of sampling events on clusters in the plurality of clusters, including using the plurality of sequences of pixel signals to classify results of the sequence of sampling events on a number N+M of clusters in the plurality of clusters from the number N of active sensors, where M is a positive integer, by classifying results for the two clusters forming a cluster pair from the sequences of pixel signals from the at least one active sensor in the array of sensors.

35. The device of clause 34, wherein the results of the sequence of sampling events correspond to nucleotide bases in the clusters, preferably wherein the first illumination stage induces illumination from a given cluster indicating nucleotide bases A and T and the second illumination stage induces illumination from a given cluster indicating nucleotide bases C and T, and said classifying results comprises calling one of the nucleotide bases A, C, T or G.

36. The device of any of clauses 34 to 35, wherein the logic to classify results for two clusters includes mapping a first pixel signal of the set of signal samples for a sampling event from a particular sensor into at least four bins, and mapping a second pixel signal of the set of signal samples for the sampling event into at least four bins, and logically combining the mapping of the first and second pixel signals to classify the results for two clusters.

37. The device of any of clauses 34 to 36, wherein the sample surface holds clusters that are distributed unevenly over the pixel areas, and the signal processor executes time sequence and spatial analysis of the plurality of sequences of pixel signals to detect patterns of illumination corresponding to individual clusters on the sample surface, and to classify the results of the sampling events for the individual clusters, wherein the plurality of sequences of pixel signals encodes differential crosstalk between at least two clusters resulting from their uneven distribution over the pixel areas.

38. The device of any of clauses 34 to 37, wherein the sample surface comprises an array of wells overlying the pixel areas, including two wells per pixel area, the two wells per pixel area including a dominant well and a subordinate well, the dominant well having a larger cross section over the pixel area than the subordinate well.

39. The device of any of clauses 34 to 38, wherein the sample surface comprises an array of wells overlying the pixel areas, and the sampling events include at least a first chemical stage with a number K of illumination stages where K is a positive integer, where the illumination stages of the K illumination stages illuminate the pixel areas with different angles of illumination, and the sequences of pixel signals include a set of signal samples for each sampling event, the set including the number K of pixel signals for the at least one chemical stage of the sampling events; wherein preferably the sampling events further include a second chemical stage with a number J of illumination stages where J is a positive integer, where the illumination stages of the K illumination stages in the first chemical stage and of the J illumination stages in the second chemical stage illuminate the wells in the array of wells with different angles of illumination, and the set of signal samples further includes the number J of pixel signals for the second chemical stage of the sampling events.

40. The device of any of clauses 34 to 39, wherein the array of sensors is included in a solid state imager.

41. The device of any of clauses 34 to 40, wherein a pixel area receives light from a well on the sample surface and the well is configured to hold more than one cluster during the base calling cycle, wherein a cluster preferably comprises a plurality of single-stranded deoxyribonucleic acid (abbreviated DNA) fragments having an identical nucleic acid sequence.

42. A computer-implemented method of base calling, including:

for a base calling cycle of a sequencing by synthesis (SBS) run, receiving from a communication port a plurality of sequences of pixel signals, the plurality of sequences of pixel signals being generated, for a sequence of sampling events comprising two illumination stages in time sequence, based on light emitted by a plurality of clusters held by a number N of pixel areas of a sample surface by an array of sensors comprising light detectors, the array having a number N of active sensors each associated with a corresponding pixel area of the N pixel areas and configured to detect light emissions gathered from the associated pixel area, the sensors being configured to generate respective pixel signals during the sequence of sampling events from the number N of corresponding pixel areas of the sample surface to produce the plurality of sequences of pixel signals, the sequences of pixel signals including at least one pixel signal for each pixel area and illumination stage, wherein at least one active sensor detects light emissions from at least two clusters forming a cluster pair of the plurality of clusters, wherein the intensity of respective light emissions of the two clusters is significantly different; and processing the plurality of sequences of pixel signals to classify results of the sequence of sampling events on clusters in the plurality of clusters, including using the plurality of sequences of pixel signals to classify results of the sequence of sampling events on clusters in the plurality of clusters, including using the plurality of sequences of pixel signals to classify results of the sequence of sampling events on a number N+M of clusters in the plurality of clusters from the number N of active sensors, where M is a positive integer, by classifying results for the two clusters forming a cluster pair from the sequences of pixel signals from the at least one active sensor in the array of sensors.

43. The computer-implemented method of clause 42, further including:

mapping a first pixel signal, which represents light gathered from a first pixel area during a first illumination stage of the base calling cycle, into at least four bins and mapping a second pixel signal, which represents light gathered from the first pixel area during a second illumination stage of the base calling cycle, into at least four bins, and combining the mapping of the first and second pixel signals to identify the incorporated nucleotide bases.

44. The computer-implemented method of any of clauses 42 to 43, further including applying the method to identify the nucleotide bases incorporated onto the plurality of clusters at a plurality of pixel areas during the base calling cycle, preferably further including repeating the method over successive base calling cycles to identify the nucleotide bases incorporated onto the plurality of clusters at the plurality of pixel areas during each of the base calling cycles, more preferably further including:

for each of the base calling cycles, detecting and storing the first and second pixel signals emitted by the plurality of clusters at the plurality of pixel areas, and after the base calling cycles, using the combination of the first and second pixel signals to identify the nucleotide bases incorporated onto the plurality of clusters at the plurality of pixel areas during each of the previous base calling cycles.

45. The computer-implemented method of any of clauses 42 to 44, wherein at least one of the following applies:

the first pixel area receives light from an associated well on a sample surface; preferably light from more than one associated well on the sample surface;

the first and second pixel signals are gathered by a first sensor from the first pixel area, wherein the first and second pixel signals are preferably detected by a signal processor configured for processing pixel signals gathered by the first sensor, and the first illumination stage induces illumination from the first and second clusters to produce emissions from labeled nucleotide bases A and T and the second illumination stage induces illumination from the first and second clusters to produce emissions from labeled nucleotide bases C and T.

46. The computer-implemented method of any of clauses 42 to 45, in which said base calling includes using a device as defined in any one of clauses 34 to 41.

47. A method of identifying pixel areas with more than one cluster on a sample surface of a biosensor and base calling clusters at the identified pixel areas, preferably the method of any of clauses 34-46, including:

performing a plurality of base calling cycles, each base calling cycle having a first illumination stage and a second illumination stage;

capturing at a sensor associated with a pixel area of the sample surface, a first set of intensity values generated during the first illumination stage of the base calling cycles, and a second set of intensity values generated during the second illumination stage of the base calling cycles;

fitting sixteen distributions to the first and second sets of intensity values using a signal processor and, based on the fitting, classifying the pixel area as having more than one cluster; and for a successive base calling cycle, detecting the first and second sets of intensity values for a cluster group at the pixel area using the signal processor, and selecting a distribution for the cluster group, wherein the distribution identifies a nucleotide base present in each cluster of the cluster group wherein preferably at least one of the following applies:

the fitting comprises using one or more algorithms, including a k-means clustering algorithm, a k-means-like clustering algorithm, an expectation maximization algorithm, and a histogram based algorithm;

the method further comprises normalizing the intensity values;

the pixel area receives light from an associated well on the sample surface; and said identifying and base calling includes using a device as defined in any one of clauses 34 to 41.

48. A computer-implemented method of base calling, preferably the method according to any of clauses 42-46, the method comprising:

providing a first pixel signal that represents light gathered from a first pixel area during a first illumination stage of a base calling cycle of a sequencing by synthesis (abbreviated SBS) run and a second pixel signal that represents light gathered from said first pixel area during a second illumination stage of said base calling cycle of said SBS run, wherein the first pixel area underlies first and second clusters that share the first pixel area;

providing a signal processor configured for processing at least said first and second pixel signals;

mapping the first pixel signal into at least four bins and mapping the second pixel signal into at least four bins using said signal processor; and logically combining the mapping of the first and second pixel signals to identify the nucleotide base incorporated onto each of said first and second clusters during said base calling cycle, or being a method of identifying pixel areas with more than one cluster on a sample surface of a biosensor and base calling clusters at the identified pixel areas, comprising:

providing a first set of intensity values generated during a first illumination stage of a base calling cycle and a second set of intensity values generated during a second illumination stage of the base calling cycle, wherein the first and second sets of intensity values represent the intensity of light gathered at a sensor associated with a pixel area of the sample surface;

fitting sixteen distributions to the first and second sets of intensity values using a signal processor and, based on the fitting, classifying the pixel area as having more than one cluster; and for a successive base calling cycle, providing first and second sets of intensity values for a cluster group at the pixel area using the signal processor, and selecting a distribution for the cluster group, wherein the distribution identifies a nucleotide base present in each cluster of the cluster group, wherein the fitting preferably comprises using one or more algorithms, including a k-means clustering algorithm, a k-means-like clustering algorithm, an expectation maximization algorithm, and a histogram based algorithm.

We claim as follows:

1. A method of decoding a sequence of first and second pixel signals to base call nucleic acids in a first cluster and a second cluster, including:

receiving a first pixel signal from a first illumination stage of a sampling event, followed by a second pixel signal from a second illumination stage of the sampling event, wherein each pixel signal includes intensity values sensed from the first and second clusters;

mapping the first and second pixel signals of the sampling event into a particular one of sixteen bins, wherein the sixteen bins represent possible combinations of bases from the first cluster and the second cluster; and generating a pair of base calls for the first and second clusters from the mapping into the particular bin.

2. The method of claim 1, further including repeatedly receiving sampling events, mapping signals and generating pairs of base calls, wherein successive sampling events correspond to successive bases in the first and second clusters.

3. The method of claim 1, wherein the sampling event comprises two illumination stages in time sequence for a single chemical stage.

4. The method of claim 1, wherein each pixel signal is collected by a sensor in an array of sensors comprising light detectors.

5. The method of claim 1, wherein the sampling event comprises two illumination stages in time sequence, and sequences of pixel signals in a plurality of sequences of pixel signals comprising a set of signal samples, the set comprising at least one pixel signal from each of the two illumination stages, and wherein the first illumination stage induces illumination from the first and second clusters indicating bases A and T and the second illumination stage induces illumination from the first and second clusters in the pixel areas of the sensors indicating bases C and T, and generating the pair of base calls comprises calling one of the bases A, C, T or G for each of the first and second clusters using at least one sequence of pixel signals.

6. The method of claim 1, wherein a sample surface holds clusters that are distributed unevenly over pixel areas, whereby intensity values from the first cluster are brighter and from the second cluster are dimmer due to their uneven distribution over the pixel areas.

7. The method of claim 1, wherein receiving each signal sample comprises receiving the intensity values from two wells overlying a pixel area, the two wells per pixel area including a dominant well holding the first cluster and a subordinate well holding the second cluster, the dominant well having a larger cross section over the pixel area than the subordinate well.

8. The method of claim 1, wherein a sample surface comprises an array of wells overlying pixel areas, and the first and second clusters are in a single well, further including the sampling event including at least one chemical stage with a number K of illumination stages where K is a positive integer greater than or equal to two, wherein the illumination stages of the K illumination stages illuminate the pixel areas with different angles of illumination, and the sequences of pixel signals include the number K of pixel signals for the at least one chemical stage of the sampling events.

9. The method of claim 1, wherein a sample surface comprises an array of wells overlying pixel areas, and the sampling events include a first chemical stage with a number K of illumination stages where K is a positive integer, and a second chemical stage with a number J of illumination stages where J is a positive integer, where the illumination stages of the K illumination stages in the first chemical stage and of the J illumination stages in the second chemical stage illuminate the wells in the array of wells with different angles of illumination, and sequences of pixel signals include the number K of pixel signals for the first chemical stage plus the number J of pixel signals for the second chemical stage of the sampling events.

10. A non-transitory computer readable medium comprising program instructions that, when executed on hardware, configure the hardware to implement actions for decoding a sequence of first and second pixel signals to base call nucleotides in a first cluster and a second cluster, the actions including:

receiving a first pixel signal from a first illumination stage of a sampling event, followed by a second pixel signal from a second illumination stage of the sampling event, wherein each pixel signal includes intensity values sensed from the first and second clusters;

mapping the first and second pixel signals of the sampling event into a particular one of sixteen bins, wherein the sixteen bins represent possible combinations of bases from the first and second clusters; and generating a pair of base calls for the first and second clusters from the mapping into the particular bin.

11. The transitory computer readable medium of claim 10, wherein the actions further including repeatedly receiving sampling events, mapping signals and generating pairs of base calls, wherein successive sampling events correspond to successive bases in the first and second clusters.

12. The transitory computer readable medium of claim 10, wherein the sampling event comprises two illumination stages in time sequence for a single chemical stage.

13. The transitory computer readable medium of claim 10, wherein each pixel signal is collected by a sensor in an array of sensors comprising light detectors.

14. The transitory computer readable medium of claim 10, wherein the sampling event comprises two illumination stages in time sequence, and sequences of pixel signals in a plurality of sequences of pixel signals comprising a set of signal samples, the set comprising at least one pixel signal from each of the two illumination stages, and wherein the first illumination stage induces illumination from one or more clusters in the pixel areas of the sensors indicating bases A and T and the second illumination stage induces illumination from one or more clusters in the pixel areas of the sensors indicating bases C and T, and generating the pair of base calls comprises calling one of the bases A, C, T or G for each of the first and second clusters using said at least one sequence of pixel signals.

15. The transitory computer readable medium of claim 10, wherein a sample surface holds clusters that are distributed unevenly over pixel areas, whereby intensity values from the first cluster are brighter and from the second cluster are dimmer due to their uneven distribution over the pixel areas.

16. The transitory computer readable medium of claim 10, wherein receiving each signal sample comprises receiving the intensity values from two wells overlying a pixel area, the two wells per pixel area including dominant well holding the first cluster and a subordinate well holding the second cluster, the dominant well having a larger cross section over the pixel area than the subordinate well.

17. The transitory computer readable medium of claim 10, wherein a sample surface comprises an array of wells overlying pixel areas, and the first and second clusters are in a single well, further including the sampling event including at least one chemical stage with a number K of illumination stages where K is a positive integer greater than or equal to two, wherein the illumination stages of the K illumination stages illuminate the pixel areas with different angles of illumination, and the sequences of pixel signals include the number K of pixel signals for the at least one chemical stage of the sampling events.

18. The transitory computer readable medium of claim 10, wherein a sample surface comprises an array of wells overlying pixel areas, and the sampling events include a first chemical stage with a number K of illumination stages where K is a positive integer, and a second chemical stage with a number J of illumination stages where J is a positive integer, where the illumination stages of the K illumination stages in the first chemical stage and of the J illumination stages in the second chemical stage illuminate the wells in the array of wells with different angles of illumination, and sequences of pixel signals include the number K of pixel signals for the first chemical stage plus the number J of pixel signals for the second chemical stage of the sampling events.

19. A system including a processor and memory coupled to the processor, the memory holding program instructions that, when executed on hardware, configure the memory and hardware to implement actions for decoding a sequence of first and second pixel signals to base call nucleic acids in a first cluster and a second cluster, the actions including:

receiving a first pixel signal from a first illumination stage of a sampling event, followed by a second pixel signal from a second illumination stage of the sampling event, wherein each pixel signal includes intensity values sensed from the first and second clusters;

mapping the first and second pixel signals of the sampling event into a particular one of sixteen bins, wherein the sixteen bins represent possible combinations of bases from the first and second clusters; and generating a pair of base calls for the first and second clusters from the mapping into the particular bin.

20. The system of claim 19, wherein the actions further including repeatedly receiving sampling events, mapping signals and generating pairs of base calls that wherein successive sampling events correspond to successive bases in the first and second clusters.

* * * * *